United States Patent
Nikolchev et al.

(10) Patent No.: US 10,799,383 B2
(45) Date of Patent: Oct. 13, 2020

(54) APPARATUS AND METHOD FOR DISTRACTING THE HIP JOINT

(71) Applicant: Stryker Corporation, Kalamazoo, MI (US)

(72) Inventors: Julian Nikolchev, Portola Valley, CA (US); William Kaiser, Campbell, CA (US); Brett Page, Sunnyvale, CA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 16/030,184

(22) Filed: Jul. 9, 2018

(65) Prior Publication Data

US 2019/0008673 A1    Jan. 10, 2019

Related U.S. Application Data

(63) Continuation of application No. 14/261,189, filed on Apr. 24, 2014, now Pat. No. 10,022,259.

(60) Provisional application No. 61/815,630, filed on Apr. 24, 2013.

(51) Int. Cl.
*A61F 5/04* (2006.01)

(52) U.S. Cl.
CPC ...................................... *A61F 5/04* (2013.01)

(58) Field of Classification Search
CPC ....... A61B 17/025; A61B 17/60; A61B 17/66; A61B 2017/0268; A61B 2017/0275; A61B 2017/603; A61B 2017/681; A61F 5/04; A61F 5/042

See application file for complete search history.

(56) References Cited

U.S. PATENT DOCUMENTS

| | | | | |
|---|---|---|---|---|
| 2,678,857 A | * | 5/1954 | Hans | A61G 13/12 5/636 |
| 4,418,422 A | * | 11/1983 | Richter | A61B 17/1703 378/162 |
| 4,624,245 A | * | 11/1986 | Mullin | A61G 13/0081 5/621 |
| 4,802,464 A | * | 2/1989 | Deprez | A61F 5/04 5/613 |
| 4,940,218 A | * | 7/1990 | Akcelrod | A61G 13/0036 5/621 |
| 5,025,802 A | * | 6/1991 | Laico | A61G 13/12 128/875 |
| 5,056,535 A | * | 10/1991 | Bonnell | A61G 13/12 128/882 |
| 5,063,918 A | * | 11/1991 | Guhl | A61B 17/6425 602/40 |
| 5,162,039 A | * | 11/1992 | Dahners | A61F 5/04 602/23 |

(Continued)

FOREIGN PATENT DOCUMENTS

WO    WO 2013/119688 A1    8/2013

*Primary Examiner* — Eric S Gibson
(74) *Attorney, Agent, or Firm* — Pandiscio & Pandiscio

(57) ABSTRACT

Apparatus for distracting the hip joint of a patient, said apparatus comprising:
a perineal post for engagement with a leg of the patient, said perineal post comprising a first portion and a second portion, wherein said first portion is configured for mounting to a table, and further wherein said second portion is movable relative to said first portion so as to change the geometry of the perineal post relative to a patient supported on the table.

20 Claims, 31 Drawing Sheets

(56) References Cited

U.S. PATENT DOCUMENTS

| | | | | |
|---|---|---|---|---|
| 5,290,220 A * | 3/1994 | Guhl | A61F 5/04 | 128/882 |
| 5,515,562 A * | 5/1996 | Miller | A61G 13/0036 | 5/624 |
| 5,658,315 A * | 8/1997 | Lamb | A61F 5/04 | 602/32 |
| 5,806,117 A * | 9/1998 | Gotfried | A61G 13/12 | 5/601 |
| 6,311,349 B1 * | 11/2001 | Kazakia | A61G 13/12 | 128/845 |
| 7,246,390 B2 * | 7/2007 | Mitsuishi | A61H 1/0237 | 5/621 |
| 7,337,483 B2 * | 3/2008 | Boucher | A61G 13/12 | 5/621 |
| 7,665,167 B2 * | 2/2010 | Branch | A61B 17/154 | 128/882 |
| 7,677,249 B2 * | 3/2010 | Kong | A61F 5/37 | 128/112.1 |
| 7,832,401 B2 * | 11/2010 | Torrie | A61G 13/0036 | 128/845 |
| 7,947,006 B2 * | 5/2011 | Torrie | A61G 13/0036 | 602/32 |
| 8,683,631 B2 * | 4/2014 | Bellows | A61G 13/0036 | 5/624 |
| 8,986,228 B2 * | 3/2015 | Auchinleck | A61B 5/1036 | 600/587 |
| 8,997,749 B2 * | 4/2015 | Drake | A61G 13/0036 | 128/845 |
| 9,173,649 B2 * | 11/2015 | Clark | A61F 5/04 | |
| 9,314,272 B1 * | 4/2016 | DeMayo | A61B 17/66 | |
| RE46,032 E * | 6/2016 | Torrie | A61H 1/0218 | |
| 9,468,577 B2 * | 10/2016 | Sluss | A61G 15/12 | |
| 9,545,351 B2 * | 1/2017 | Sommer | A61G 13/0036 | |
| 2002/0023298 A1 | 2/2002 | Lamb et al. | | |
| 2002/0157186 A1 * | 10/2002 | VanSteenburg | A61G 13/04 | 5/621 |
| 2003/0178027 A1 * | 9/2003 | DeMayo | A61G 13/12 | 128/845 |
| 2004/0133979 A1 * | 7/2004 | Newkirk | A61G 13/0036 | 5/600 |
| 2004/0133983 A1 * | 7/2004 | Newkirk | A61G 13/0036 | 5/624 |
| 2004/0260299 A1 * | 12/2004 | Fu Kong | A61F 5/37 | 606/86 R |
| 2006/0185090 A1 | 8/2006 | Jackson | | |
| 2007/0185418 A1 * | 8/2007 | Mitsuishi | A61F 5/04 | 601/34 |
| 2007/0251011 A1 * | 11/2007 | Matta | A61G 13/0036 | 5/624 |
| 2007/0265635 A1 * | 11/2007 | Torrie | A61G 13/0036 | 606/105 |
| 2010/0154121 A1 | 6/2010 | Swain, Jr. | | |
| 2010/0249793 A1 * | 9/2010 | Truckai | A61B 17/8836 | 606/92 |
| 2011/0023893 A1 * | 2/2011 | Striggow | A61G 13/12 | 128/882 |
| 2011/0099720 A1 * | 5/2011 | Wyslucha | A61G 13/0036 | 5/658 |
| 2011/0190676 A1 | 8/2011 | Torrie et al. | | |
| 2012/0240938 A1 * | 9/2012 | Pamichev | A61G 13/101 | 128/845 |
| 2012/0259343 A1 * | 10/2012 | Clark | A61F 5/04 | 606/90 |
| 2013/0072822 A1 * | 3/2013 | Auchinleck | A61B 5/1036 | 600/595 |
| 2013/0081635 A1 * | 4/2013 | Drake | A61G 13/0036 | 128/845 |
| 2013/0199541 A1 * | 8/2013 | Sluss | A61G 13/12 | 128/845 |
| 2014/0324056 A1 * | 10/2014 | Nikolchev | A61F 5/04 | 606/90 |
| 2015/0057668 A1 * | 2/2015 | Chehab | A61B 17/025 | 606/90 |
| 2015/0245971 A1 * | 9/2015 | Bernardoni | A61G 13/0036 | 5/601 |
| 2015/0290064 A1 * | 10/2015 | Kreuzer | A61G 13/02 | 128/845 |
| 2016/0287237 A1 * | 10/2016 | DeMayo | A61G 13/0036 | |
| 2017/0014256 A1 * | 1/2017 | McGraw | A61F 5/042 | |
| 2017/0042581 A1 * | 2/2017 | Torrie | A61G 13/0036 | |
| 2019/0008673 A1 * | 1/2019 | Nikolchev | A61F 5/04 | |

\* cited by examiner

CAM-TYPE FEMOROACETABULAR IMPINGEMENT (FAI)

CAM INJURY TO THE LABRUM

PINCER-TYPE FEMOROACETABULAR IMPINGEMENT (FAI)

PINCER INJURY TO THE LABRUM

APPARATUS AND METHOD FOR DISTRACTING THE HIP JOINT

REFERENCE TO PENDING PRIOR PATENT APPLICATIONS

This patent application is a continuation of pending prior U.S. patent application Ser. No. 14/261,189, filed Apr. 24, 2014 by Pivot Medical, Inc. for APPARATUS AND METHOD FOR DISTRACTING THE HIP JOINT, which in turn claims benefit of prior U.S. Provisional Patent Application Ser. No. 61/815,630, filed Apr. 24, 2013 by Pivot Medical, Inc. and Julian Nikolchev et al. for INSTRUMENTED PERINEAL POST DISTRACTION.

The two (2) above-identified patent applications are hereby incorporated herein by reference.

FIELD OF THE INVENTION

This invention relates to medical apparatus and procedures in general, and more particularly to apparatus and methods for distracting the hip joint.

BACKGROUND OF THE INVENTION

The Hip Joint in General

The hip joint is a ball-and-socket joint which movably connects the leg to the torso. The hip joint is capable of a wide range of different motions, e.g., flexion and extension, abduction and adduction, medial and lateral rotation, etc. See FIGS. 1A, 1B, 1C and 1D.

With the possible exception of the shoulder joint, the hip joint is perhaps the most mobile joint in the body. Significantly, and unlike the shoulder joint, the hip joint carries substantial weight loads during most of the day, in both static (e.g., standing and sitting) and dynamic (e.g., walking and running) conditions.

The hip joint is susceptible to a number of different pathologies. These pathologies can have both congenital and injury-related origins. In some cases, the pathology can be substantial at the outset. In other cases, the pathology may be minor at the outset but, if left untreated, may worsen over time. More particularly, in many cases, an existing pathology may be exacerbated by the dynamic nature of the hip joint and the substantial weight loads imposed on the hip joint.

The pathology may, either initially or thereafter, significantly interfere with patient comfort and lifestyle. In some cases, the pathology can be so severe as to require partial or total hip replacement. A number of procedures have been developed for treating hip pathologies short of partial or total hip replacement, but these procedures are generally limited in scope due to the significant difficulties associated with treating the hip joint.

A better understanding of various hip joint pathologies, and also the current limitations associated with their treatment, can be gained from a more thorough understanding of the anatomy of the hip joint.

Anatomy of the Hip Joint

The hip joint is formed at the junction of the leg and the hip. More particularly, and looking now at FIG. 2, the head of the femur is received in the acetabular cup of the hip, with a plurality of ligaments and other soft tissue serving to hold the bones in articulating condition.

More particularly, and looking now at FIG. 3, the femur is generally characterized by an elongated body terminating, at its top end, in an angled neck which supports a hemispherical head (also sometimes referred to as "the ball"). As seen in FIGS. 3 and 4, a large projection known as the greater trochanter protrudes laterally and posteriorly from the elongated body adjacent to the neck of the femur. A second, somewhat smaller projection known as the lesser trochanter protrudes medially and posteriorly from the elongated body adjacent to the neck. An intertrochanteric crest (FIGS. 3 and 4) extends along the periphery of the femur, between the greater trochanter and the lesser trochanter.

Looking next at FIG. 5, the hip socket is made up of three constituent bones: the ilium, the ischium and the pubis. These three bones cooperate with one another (they typically ossify into a single "hip bone" structure by the age of 25 or so) in order to collectively form the acetabular cup. The acetabular cup receives the head of the femur.

Both the head of the femur and the acetabular cup are covered with a layer of articular cartilage which protects the underlying bone and facilitates motion. See FIG. 6.

Various ligaments and soft tissue serve to hold the ball of the femur in place within the acetabular cup. More particularly, and looking now at FIGS. 7 and 8, the ligamentum teres extends between the ball of the femur and the base of the acetabular cup. As seen in FIGS. 8 and 9, a labrum is disposed about the perimeter of the acetabular cup. The labrum serves to increase the depth of the acetabular cup and effectively establishes a suction seal between the ball of the femur and the rim of the acetabular cup, thereby helping to hold the head of the femur in the acetabular cup. In addition to the foregoing, and looking now at FIG. 10, a fibrous capsule extends between the neck of the femur and the rim of the acetabular cup, effectively sealing off the ball-and-socket members of the hip joint from the remainder of the body. The foregoing structures (i.e., the ligamentum teres, the labrum and the fibrous capsule) are encompassed and reinforced by a set of three main ligaments (i.e., the iliofemoral ligament, the ischiofemoral ligament and the pubofemoral ligament) which extend between the femur and the perimeter of the hip socket. See, for example, FIGS. 11 and 12, which show the iliofemoral ligament, with FIG. 11 being an anterior view and FIG. 12 being a posterior view.

Pathologies of the Hip Joint

As noted above, the hip joint is susceptible to a number of different pathologies. These pathologies can have both congenital and injury-related origins.

By way of example but not limitation, one important type of congenital pathology of the hip joint involves impingement between the neck of the femur and the rim of the acetabular cup. In some cases, and looking now at FIG. 13, this impingement can occur due to irregularities in the geometry of the femur. This type of impingement is sometimes referred to as cam-type femoroacetabular impingement (i.e., cam-type FAI). In other cases, and looking now at FIG. 14, the impingement can occur due to irregularities in the geometry of the acetabular cup. This latter type of impingement is sometimes referred to as pincer-type femoroacetabular impingement (i.e., pincer-type FAI). Impingement can result in a reduced range of motion, substantial pain and, in some cases, significant deterioration of the hip joint.

By way of further example but not limitation, another important type of congenital pathology of the hip joint involves defects in the articular surface of the ball and/or the articular surface of the acetabular cup. Defects of this type sometimes start out fairly small but often increase in size over time, generally due to the dynamic nature of the hip joint and also due to the weight-bearing nature of the hip joint. Articular defects can result in substantial pain, induce and/or exacerbate arthritic conditions and, in some cases, cause significant deterioration of the hip joint.

By way of further example but not limitation, one important type of injury-related pathology of the hip joint involves trauma to the labrum. More particularly, in many cases, an accident or sports-related injury can result in the labrum being torn away from the rim of the acetabular cup, typically with a tear running through the body of the labrum. See FIG. 15. These types of injuries can be very painful for the patient and, if left untreated, can lead to substantial deterioration of the hip joint.

The General Trend Toward Treating Joint Pathologies Using Minimally-Invasive, and Earlier, Interventions The current trend in orthopedic surgery is to treat joint pathologies using minimally-invasive techniques. Such minimally-invasive, "keyhole" surgeries generally offer numerous advantages over traditional, "open" surgeries, including reduced trauma to tissue, less pain for the patient, faster recuperation times, etc.

By way of example but not limitation, it is common to re-attach ligaments in the shoulder joint using minimally-invasive, "keyhole" techniques which do not require laying open the capsule of the shoulder joint. By way of further example but not limitation, it is common to repair torn meniscal cartilage in the knee joint, and/or to replace ruptured ACL ligaments in the knee joint, using minimally-invasive techniques.

While such minimally-invasive approaches can require additional training on the part of the surgeon, such procedures generally offer substantial advantages for the patient and have now become the standard of care for many shoulder joint and knee joint pathologies.

In addition to the foregoing, in view of the inherent advantages and widespread availability of minimally-invasive approaches for treating pathologies of the shoulder joint and knee joint, the current trend is to provide such treatment much earlier in the lifecycle of the pathology, so as to address patient pain as soon as possible and so as to minimize any exacerbation of the pathology itself. This is in marked contrast to traditional surgical practices, which have generally dictated postponing surgical procedures as long as possible so as to spare the patient from the substantial trauma generally associated with invasive surgery.

Treatment for Pathologies of the Hip Joint

Unfortunately, minimally-invasive treatments for pathologies of the hip joint have lagged far behind minimally-invasive treatments for pathologies of the shoulder joint and the knee joint. This is generally due to (i) the constrained geometry of the hip joint itself, and (ii) the nature and location of the pathologies which must typically be addressed in the hip joint.

More particularly, the hip joint is generally considered to be a "tight" joint, in the sense that there is relatively little room to maneuver within the confines of the joint itself. This is in marked contrast to the shoulder joint and the knee joint, which are generally considered to be relatively "spacious" joints (at least when compared to the hip joint). As a result, it is relatively difficult for surgeons to perform minimally-invasive procedures on the hip joint.

Furthermore, the pathways for entering the interior of the hip joint (i.e., the natural pathways which exist between adjacent bones and/or delicate neurovascular structures) are generally much more constraining for the hip joint than for the shoulder joint or the knee joint. This limited access further complicates effectively performing minimally-invasive procedures on the hip joint.

In addition to the foregoing, the nature and location of the pathologies of the hip joint also complicate performing minimally-invasive procedures on the hip joint. By way of example but not limitation, consider a typical detachment of the labrum in the hip joint. In this situation, instruments must generally be introduced into the joint space using an angle of approach which is offset from the angle at which the instrument addresses the tissue. This makes drilling into bone, for example, significantly more complicated than where the angle of approach is effectively aligned with the angle at which the instrument addresses the tissue, such as is frequently the case in the shoulder joint. Furthermore, the working space within the hip joint is typically extremely limited, further complicating repairs where the angle of approach is not aligned with the angle at which the instrument addresses the tissue.

As a result of the foregoing, minimally-invasive hip joint procedures are still relatively difficult to perform and relatively uncommon in practice. Consequently, patients are typically forced to manage their hip pain for as long as possible, until a resurfacing procedure or a partial or total hip replacement procedure can no longer be avoided. These procedures are generally then performed as a highly-invasive, open procedure, with all of the disadvantages associated with highly-invasive, open procedures.

As a result, there is, in general, a pressing need for improved methods and apparatus for treating pathologies of the hip joint.

Current Approaches for Hip Joint Distraction

During arthroscopic hip surgery, it is common to distract the hip joint so as to provide increased workspace within the joint. More particularly, during arthroscopic hip surgery, it is common to unseat the ball of the femur from the socket of the acetabular cup so as to provide (i) improved access to the interior of the joint, (ii) additional workspace within the interior of the joint, and (iii) increased visibility for the surgeon during the procedure. This hip joint distraction is normally accomplished in the same manner that the hip joint is distracted during a total hip replacement procedure, e.g., by applying an external distraction device to the lower end of the patient's leg near the ankle and then using the external distraction device to pull the leg distally with substantial force so as to unseat the ball of the femur from the acetabular cup.

However, since the distracting force is applied to the lower end of the patient's leg, this approach necessitates that the distracting force be applied across substantially the entire length of the leg. As a result, the intervening tissue (i.e., the tissue located between where the distracting force is applied and the ball of the femur) must bear the distracting load for the entire time that the hip joint is distracted.

In practice, it has been found that the longer the distracting load is maintained on the leg, the greater the trauma imposed on the intervening tissue. Specifically, it has been found that temporary or even permanent neurological damage can occur if the leg is distracted for too long using conventional distraction techniques.

As a result, the standard of care in the field is for the surgeon to limit the duration of distraction during arthroscopic hip surgery to 90 minutes or less in order to minimize damage to the intervening tissue due to joint distraction. In some situations, this can mean that desirable therapeutic procedures may be curtailed, or even eliminated entirely, in order to keep the duration of the distraction to 90 minutes or less. And even where the duration of the distraction is kept to 90 minutes or less, significant complications can nonetheless occur for many patients.

In addition to the foregoing, in current hip distraction, it is common to use a perineal post to facilitate hip distraction. More particularly, and looking now at FIG. 16, a perineal post is generally positioned between the legs of the patient so that the medial side of the femur which is to be distracted lies against the perineal post. After the patient's leg is pulled distally (i.e., in the direction of the pulling vector $V_P$), the leg is adducted so as to lever the leg against the perineal post, which moves the neck and ball of the femur in the direction of the lateral vector $V_L$; the combination of these two displacements is $V_D$ (i.e., the resultant vector of the vectors of $V_L$ and $V_P$). This ensures that the ball of the femur is unseated from the acetabular cup in the desired direction (i.e., in the direction of the resultant vector $V_D$).

Unfortunately, it has been found that the use of a perineal post can contribute to the damage done to the intervening tissue when the leg is distracted for too long a time. This is because the perineal post can press against the pudendal nerve and/or the sciatic nerve (as well as other anatomy) when such distraction occurs. Thus, if the distraction is held too long, neurological damage can occur. This is another reason that the standard of care in the field is for the surgeon to limit the duration of distraction during arthroscopic hip surgery to 90 minutes or less (i.e., in order to minimize the risk of tissue damage due to distraction). Additionally, the perineal post can exert pressure on the blood vessels in the leg, and it has been shown that blood flow in these vessels (e.g., the femoral vein, etc.) may be significantly reduced, or in some cases completely occluded, while the hip is in distraction, thus placing the patient in danger of forming deep vein thrombosis or developing other complications.

Additionally, current hip distraction using an external distraction device limits the extent to which the leg can be manipulated under distraction during hip arthroscopy, since a substantial pulling force must be maintained on the distal end of the leg throughout the duration of the distraction. Due to this, and due to the fact that there are typically only 2-4 portals available for arthroscopic access into the interior of the hip joint, visualization and access to hip joint pathology and anatomy is frequently hindered while the leg is externally distracted. This can limit the extent of surgical procedures available to the surgeon, and can prevent some procedures from being attempted altogether. Procedures such as mosaicplasty and autologous cartilage injection are examples of procedures which require access to extensive areas of the articular surfaces of the femoral head, but which are typically not performed arthroscopically because of the aforementioned access limitations when the leg is being distracted using an external distraction device.

Thus, there is a need for a new and improved approach for distracting the hip joint which addresses some or all of the foregoing problems associated with the prior art.

Among other things, it would be beneficial for the new and improved approach to:

create a distracted space of significant size so as to allow for treatment of the central compartment of the hip joint;

minimize the pressure applied to soft tissue, nerve and vascular structures, and thereby minimize the risk of nerve palsies and thrombosis;

minimize the forces transmitted through other healthy anatomical structures such as the knee and ankle, thereby minimizing the risk of complications;

more efficiently focus the traction forces on the hip joint;

allow for variation in the applied traction vector so as to (i) accommodate patients with differences in anatomy (i.e., differences in boney structure, the strength of soft tissue, the tension of capsule tissue, etc.), and (ii) provide surgical access to different parts of the hip joint (i.e., anterior, posterior and lateral regions)—thereby effectively resulting in customized traction for each patient;

provide an apparatus with a more intuitive way to apply traction, utilizing simple controls to apply/remove traction during a procedure; and/or provide the surgeon with feedback during the procedure, so that the surgeon can better understand the effects of traction and the procedure on the patient (e.g., the traction force applied, pressure on anatomy, blood flow to the leg, temperature of the tissue, extravasation of flushing fluid from the hip joint, changes in nerve conduction, time under traction, etc.).

SUMMARY OF THE INVENTION

The present invention provides a new and improved approach for distracting the hip joint which addresses one or more of the foregoing problems associated with the prior art.

In one preferred form of the invention, there is provided apparatus for distracting the hip joint of a patient, said apparatus comprising:

a perineal post for engagement with a leg of the patient, said perineal post comprising a first portion and a second portion, wherein said first portion is configured for mounting to a table, and further wherein said second portion is movable relative to said first portion so as to change the geometry of the perineal post relative to a patient supported on the table.

In another preferred form of the invention, there is provided a method for distracting the hip joint of a patient, said method comprising:

providing apparatus comprising:
a perineal post comprising a first portion and a second portion, wherein said first portion is configured for mounting to a table, and further wherein said second portion is movable relative to said first portion;

mounting said perineal post to the table, and positioning the patient on the table so that said perineal post contacts the leg of the patient; and using the perineal post so as to distract the hip joint of the patient.

In another preferred form of the invention, there is provided a method for distracting the hip joint of a patient, the method comprising:

mounting a perineal post to a table, and positioning the patient on the table;

moving at least a portion of the perineal post; and apply a distracting force to the leg of the patient using the perineal post.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The present invention provides a new and improved approach for distracting the hip joint which addresses one or more of the foregoing problems associated with the prior art.

Dynamic Perineal Post

Figure 1A:
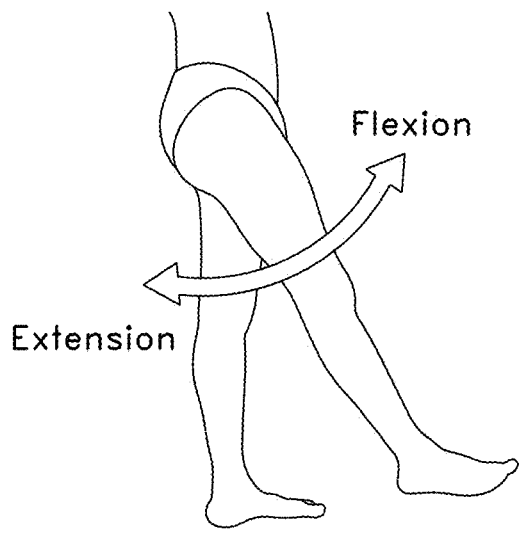
FIGS. 1A-1D are schematic views showing various aspects of hip motion.
Figure 1B:
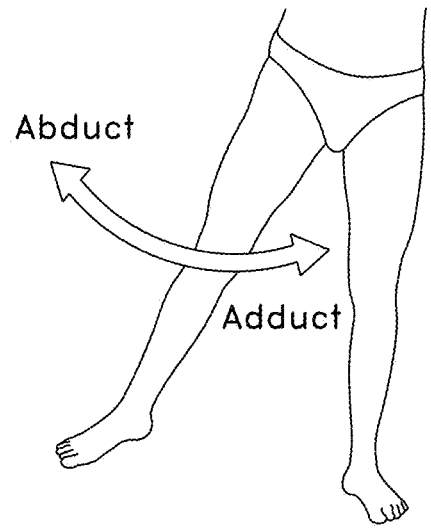
Figure 1C:
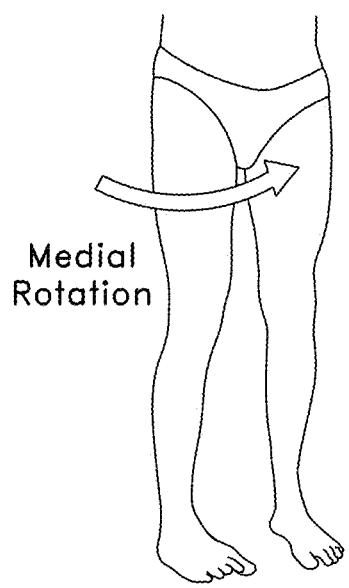
Figure 1D:
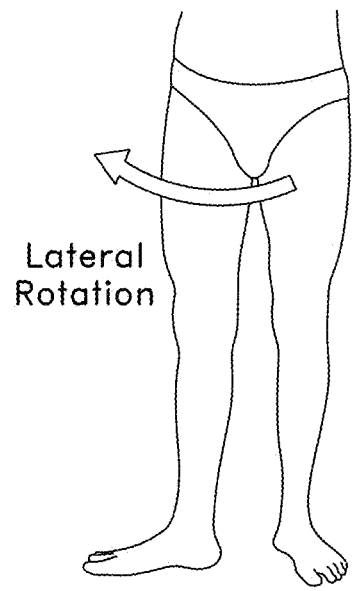
Figure 2:
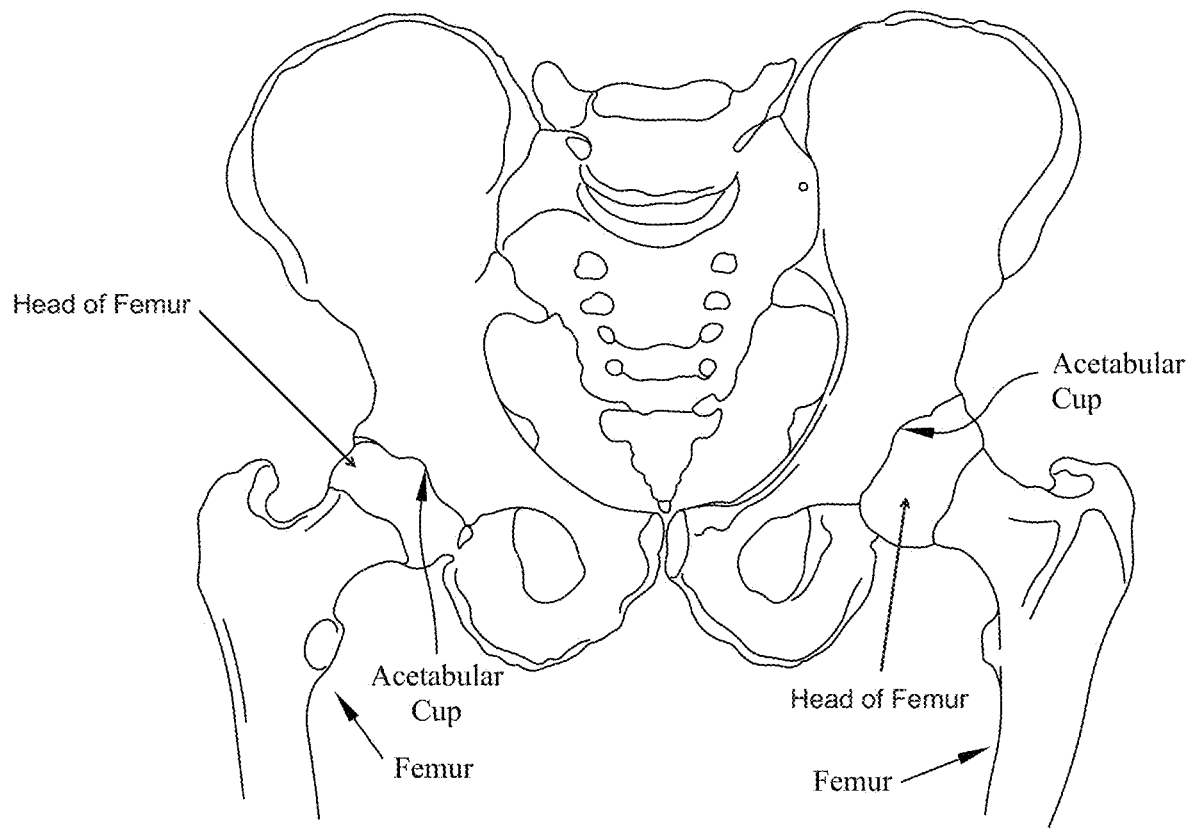
FIG. 2 is a schematic view showing bone structures in the region of the hip joint.
Figure 3:
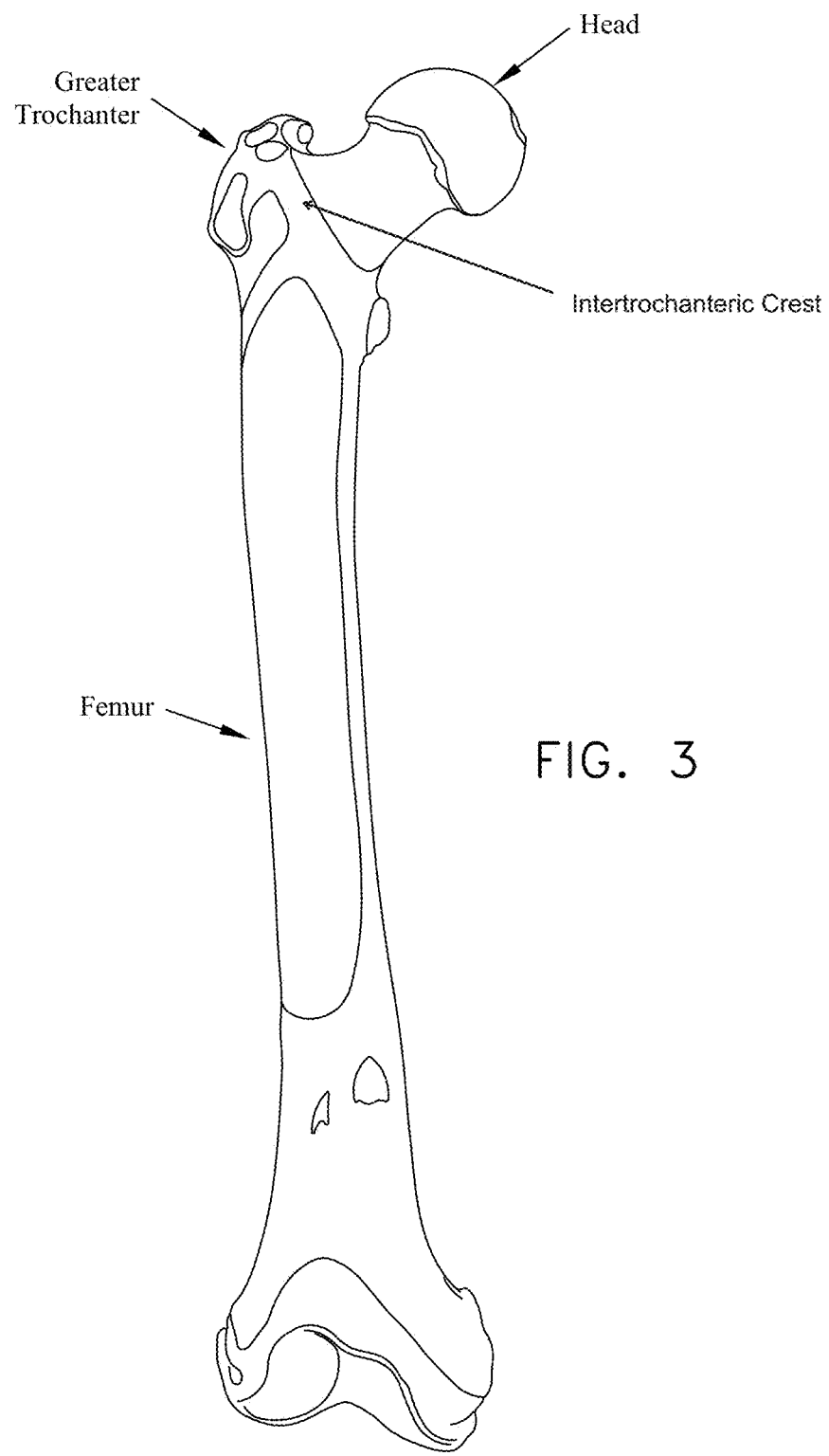
FIG. 3 is a schematic anterior view of the femur.
Figure 4:
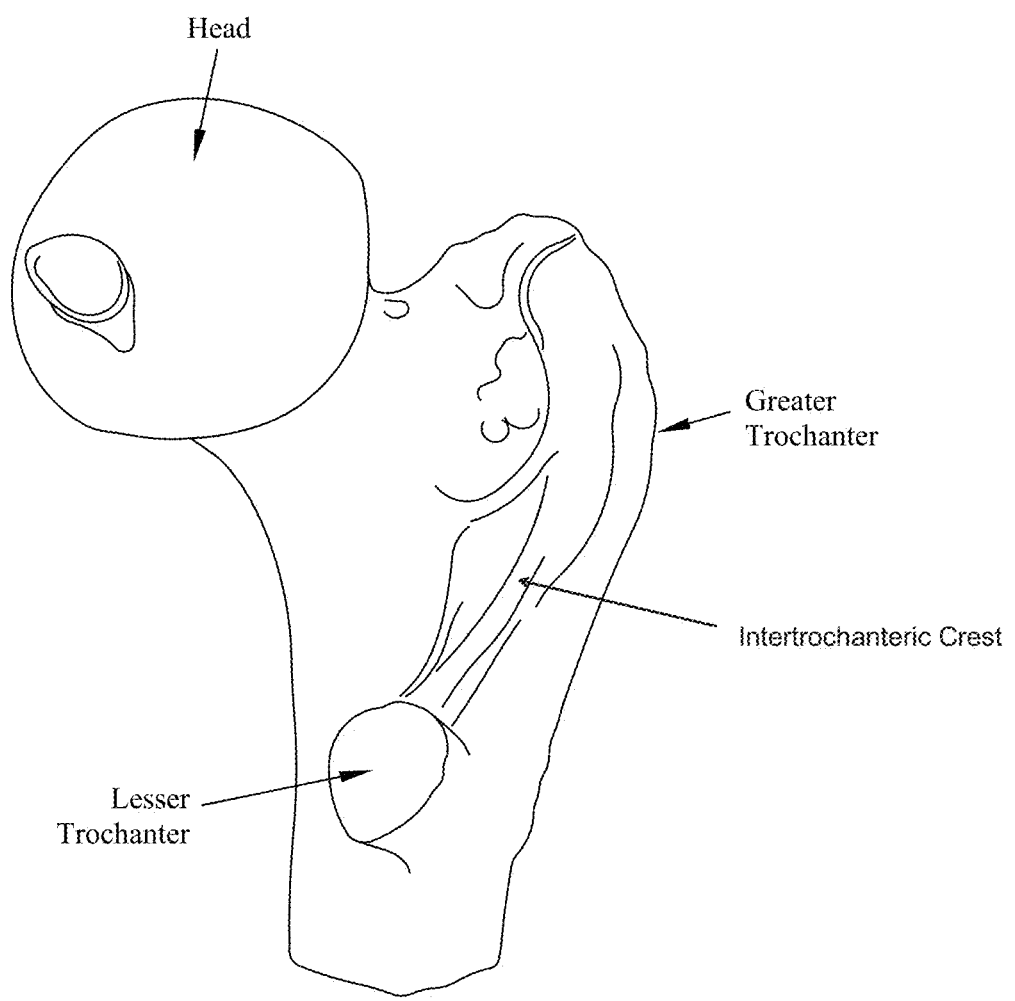
FIG. 4 is a schematic posterior view of the top end of the femur.
Figure 5:
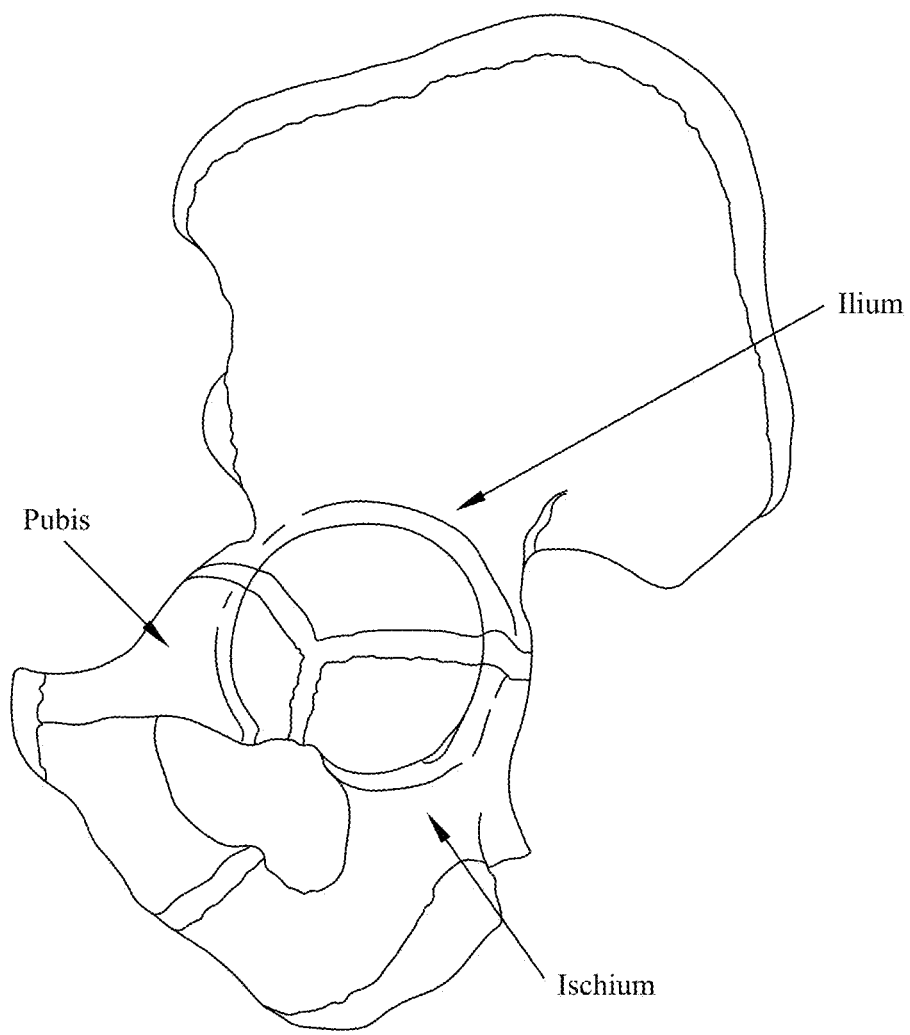
FIG. 5 is a schematic view of the pelvis.
Figure 6:
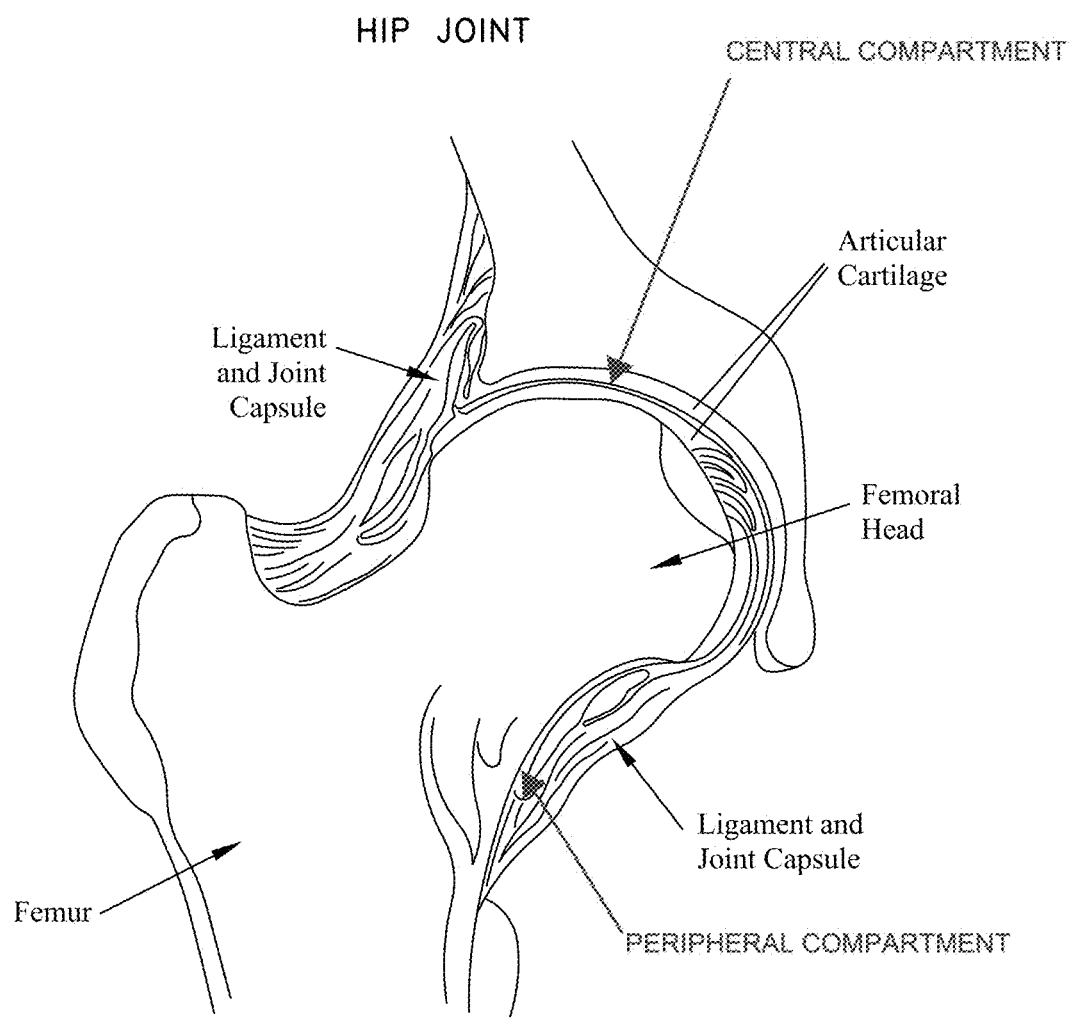
FIGS. 6-12 are schematic views showing bone and soft tissue structures in the region of the hip joint.
Figure 7:
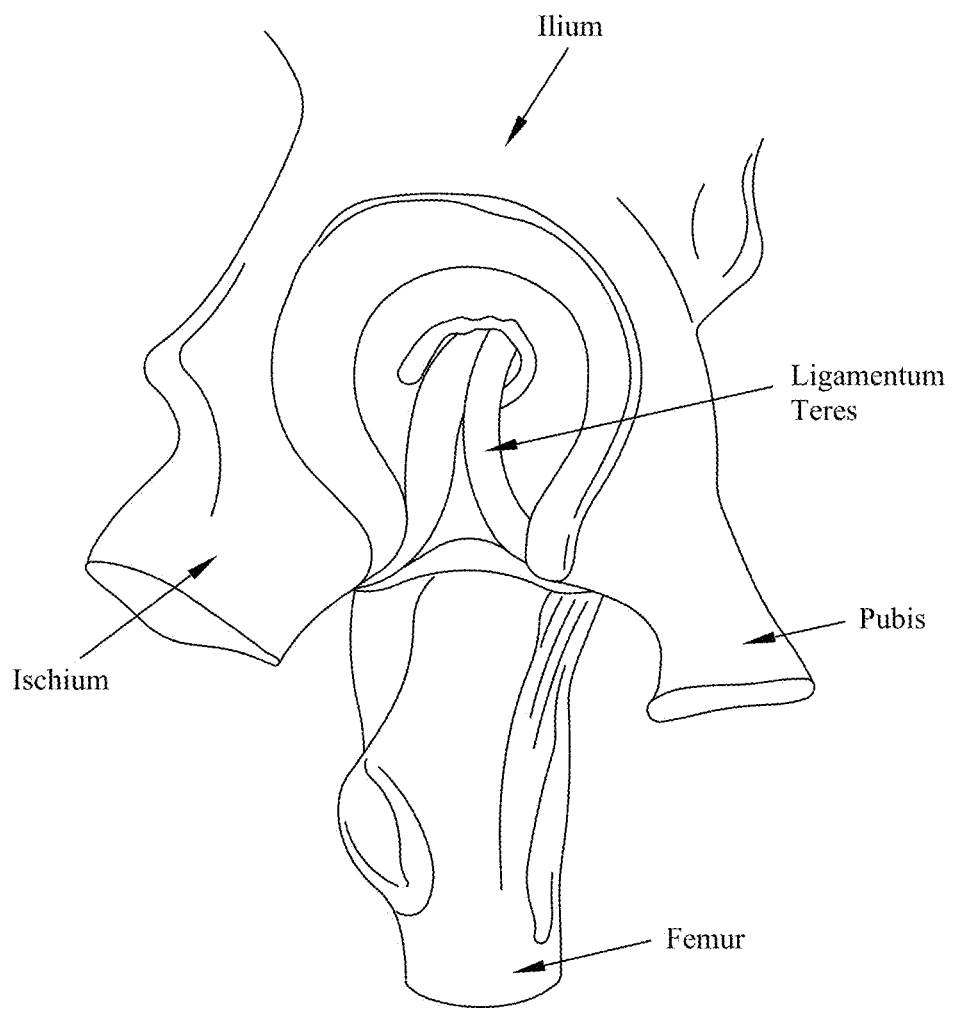
Figure 8:
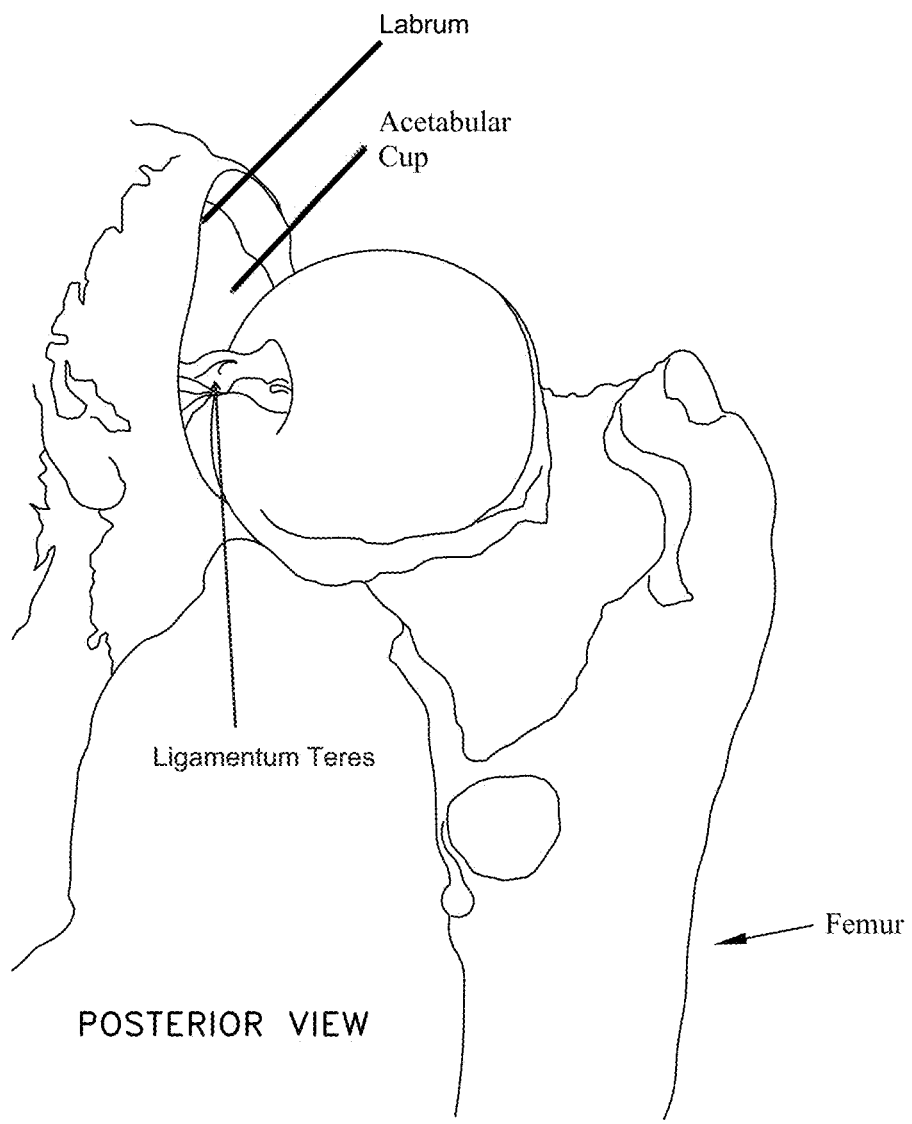
Figure 9:
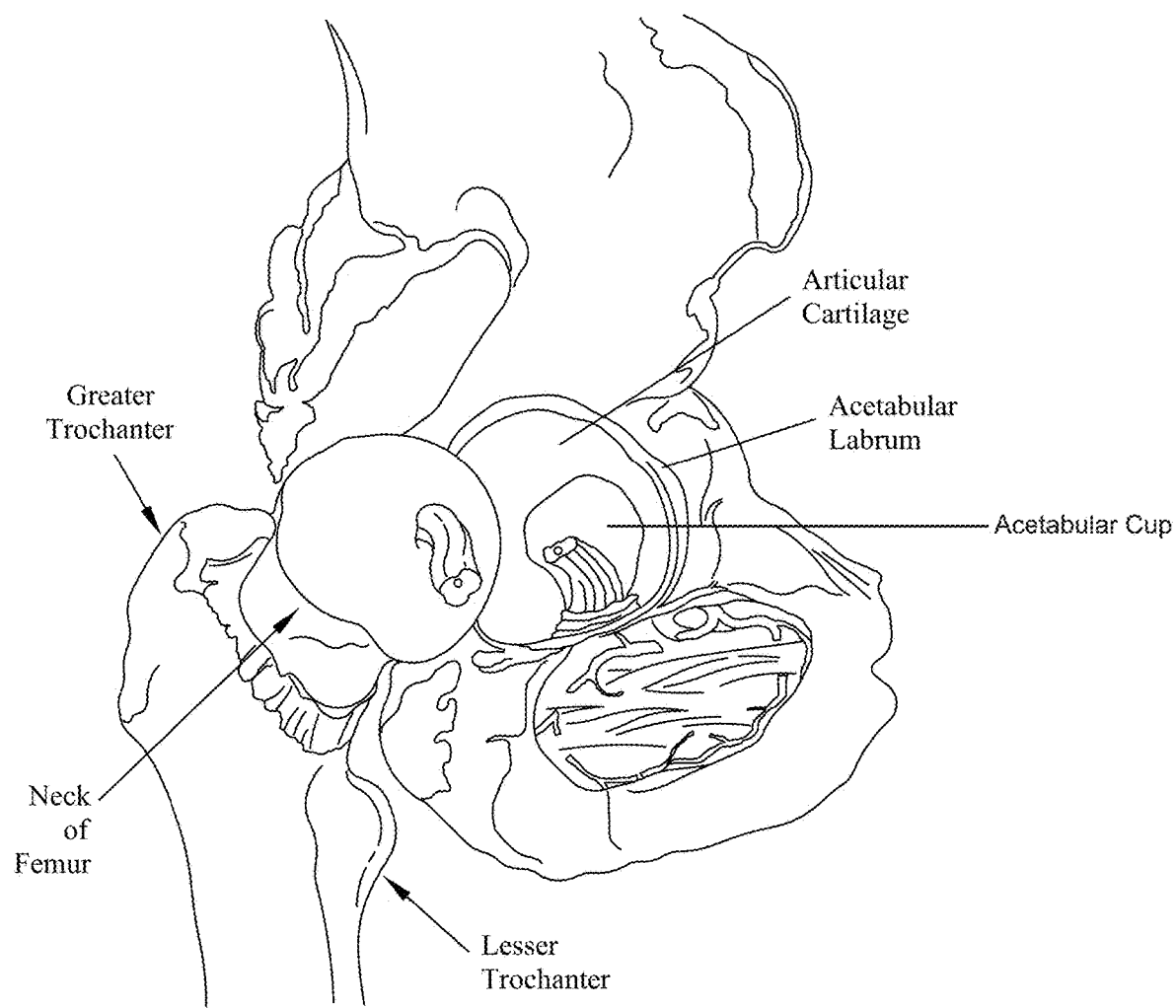
Figure 10:
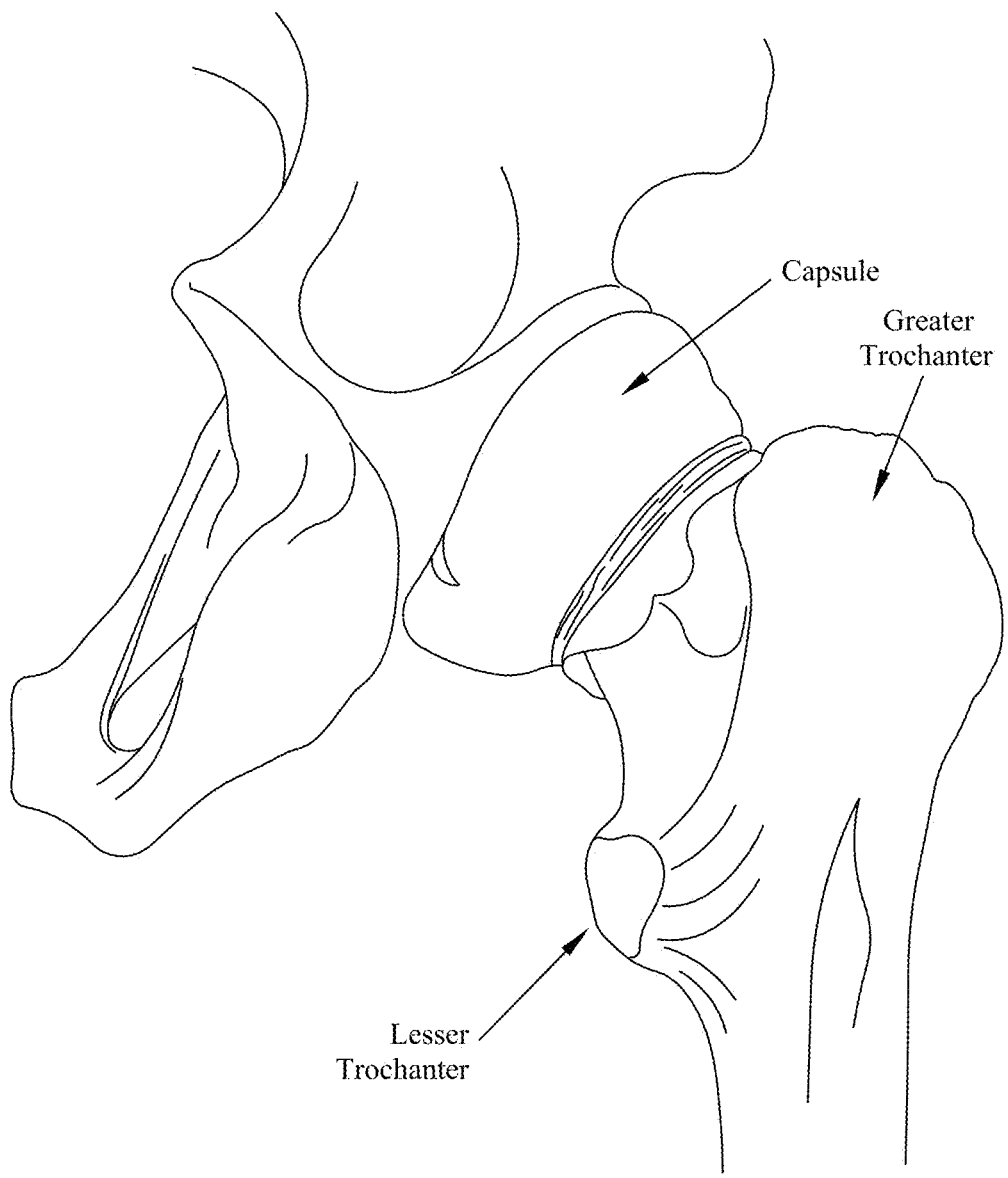
Figure 11:
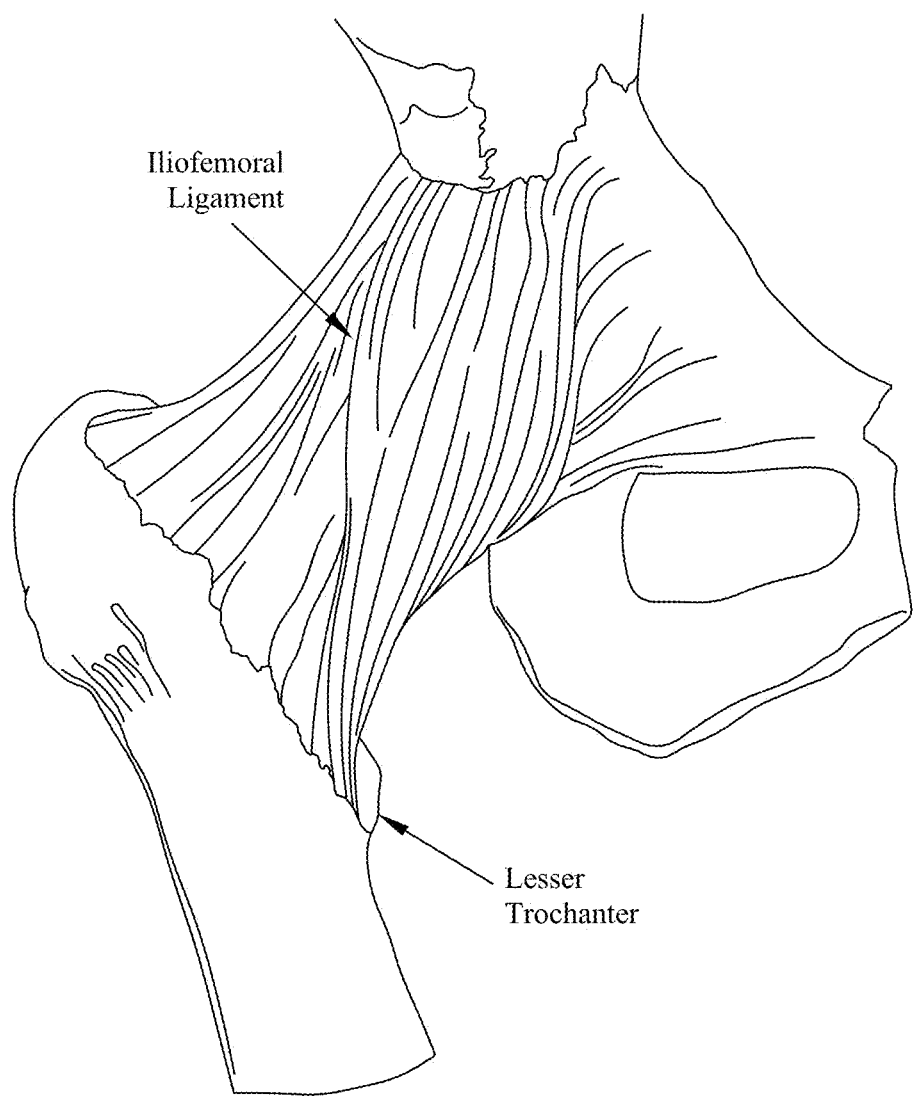
Figure 12:
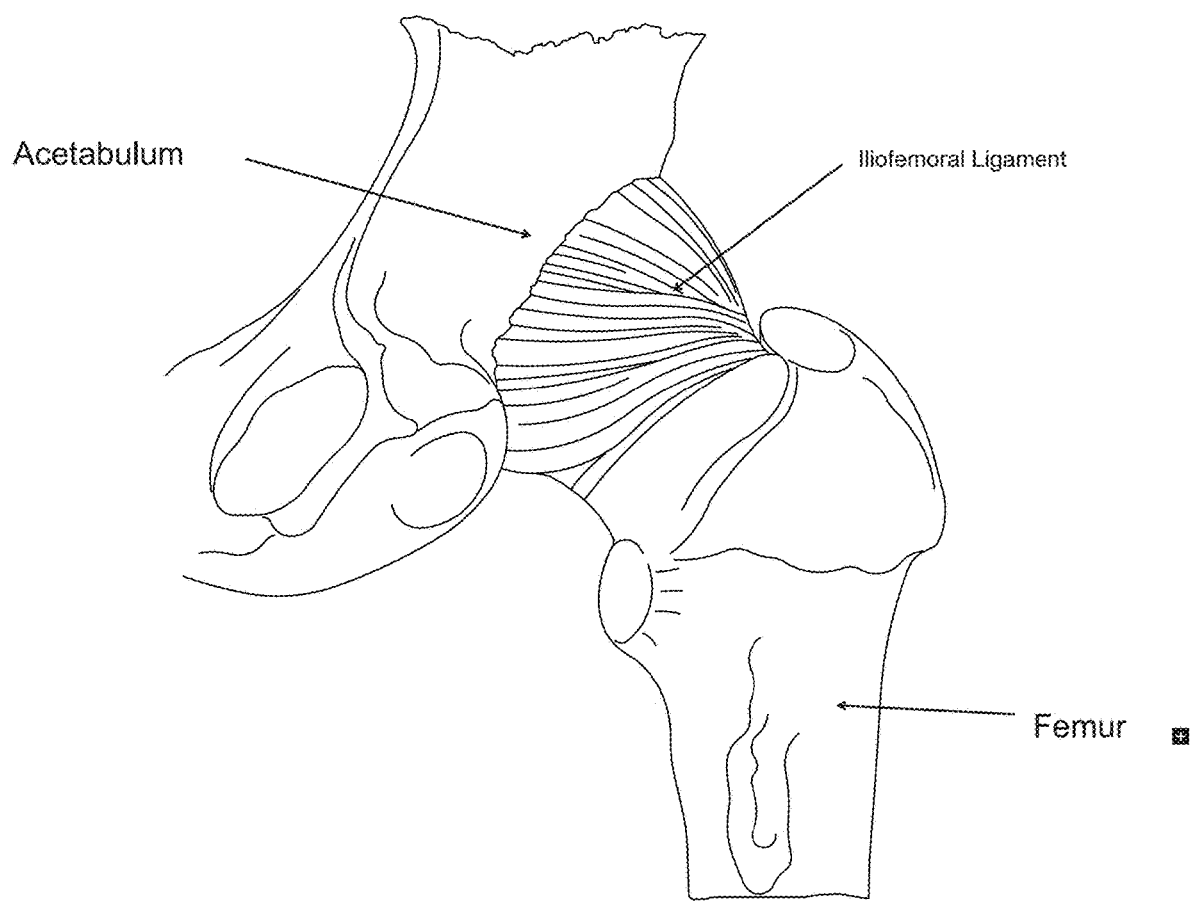
Figure 13:
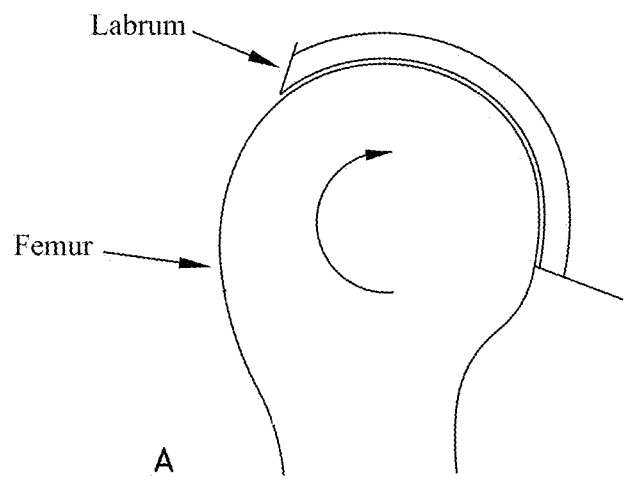
FIG. 13 is a schematic view showing cam-type femoroacetabular impingement (i.e., cam-type FAI)
Figure 13:
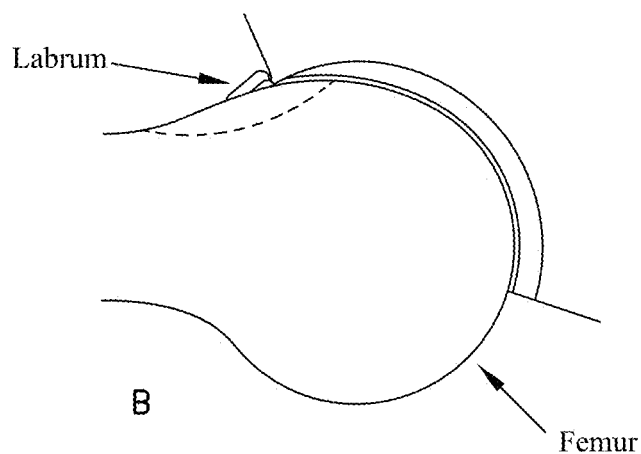
Figure 14:
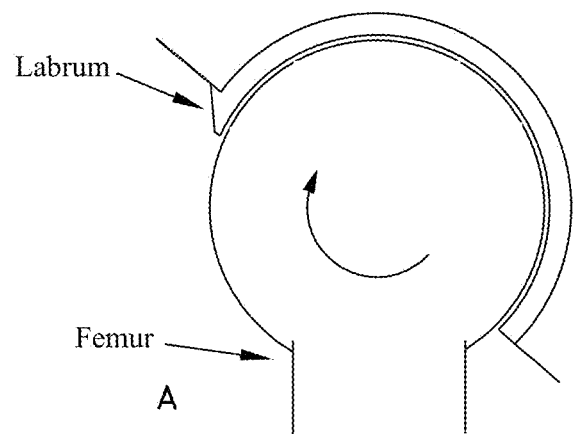
FIG. 14 is a schematic view showing pincer-type femoroacetabular impingement (i.e., pincer-type FAI)
Figure 14:
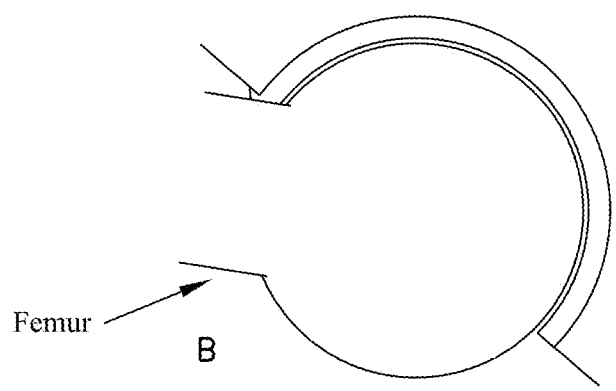
Figure 15:
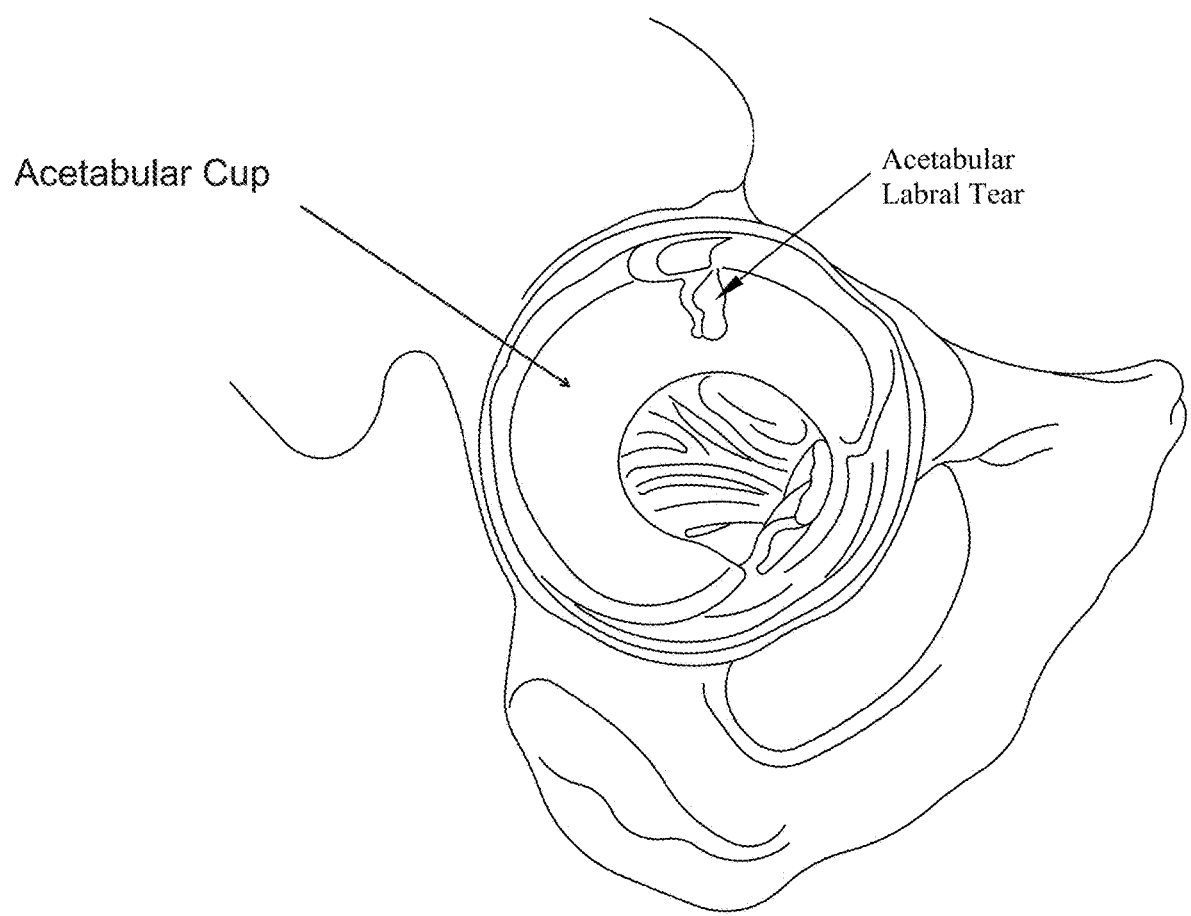
FIG. 15 is a schematic view showing a labral tear.
Figure 16:
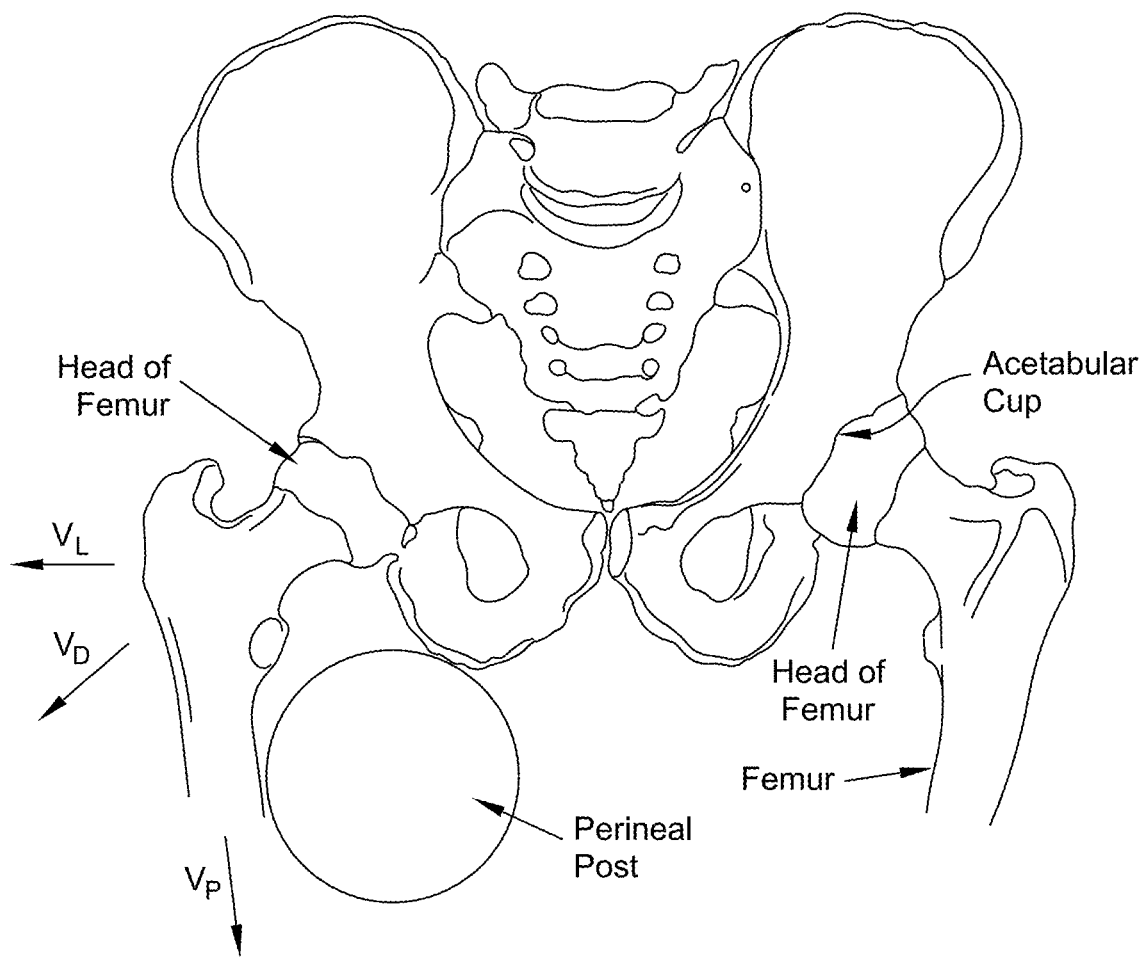
FIG. 16 is a schematic view showing a conventional perineal post set adjacent to the hip joint of a patient.
Figure 17:
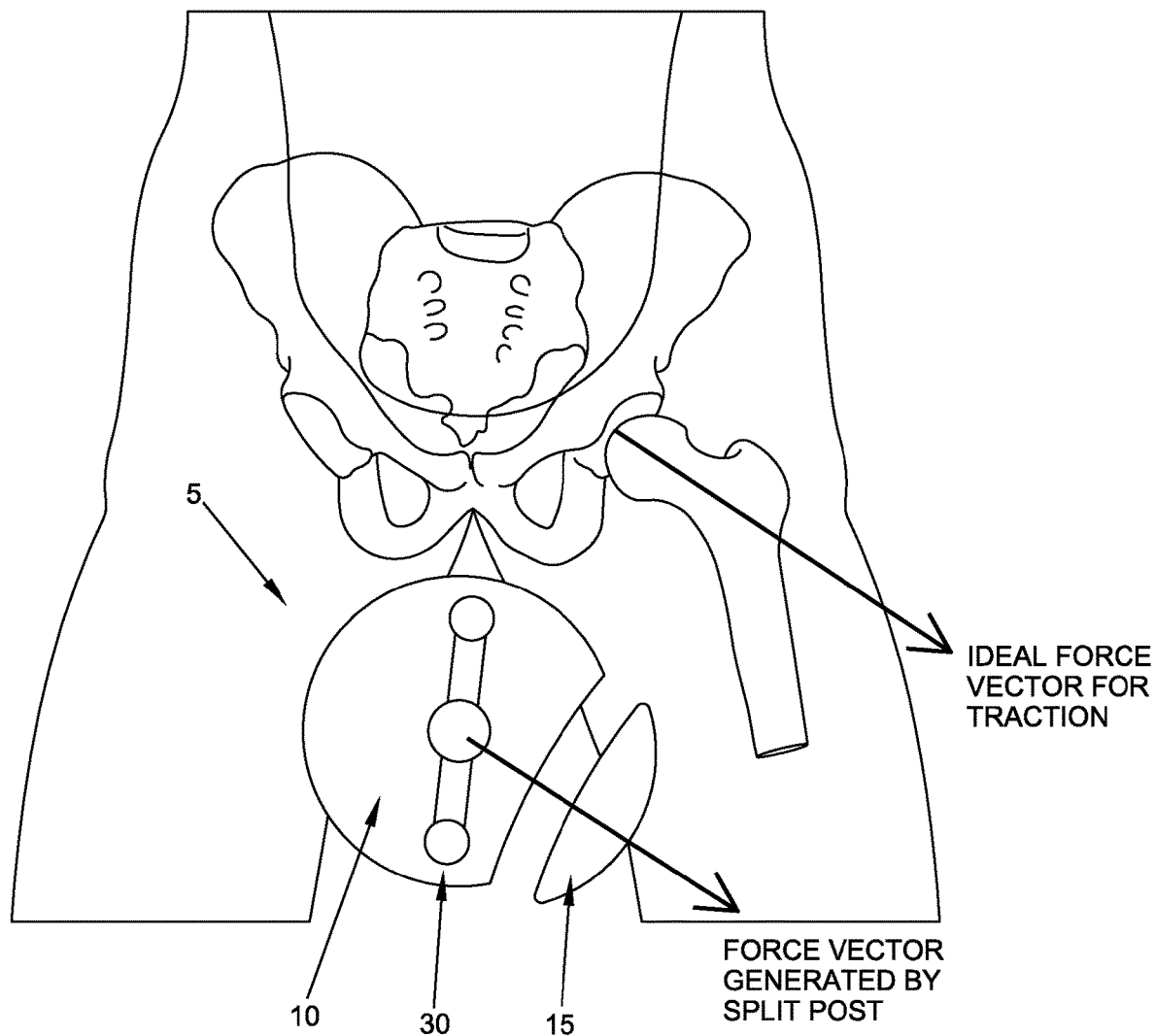
FIGS. 17-21 are schematic views showing a "dynamic" perineal post formed in accordance with the present invention.

Looking first at FIGS. 17-21, there is shown a novel perineal post 5 formed in accordance with the present invention. Perineal post 5 comprises a generally cylindrical structure having a first portion 10 and a second portion 15, wherein second portion 15 can be selectively moved away from first portion 10 so as to facilitate the application of a distracting force to the leg of the patient. Among other things, in one form of the invention, second portion 15 can be selectively moved away from first portion 10 so as to directly apply a force to the patient's leg, with the force being applied parallel to the neck of the femur of the patient, as shown in FIG. 17, whereby to create distraction of the hip joint. In another form of the invention, second portion 15 can be selectively moved away from first portion 10 so as to modify the geometry of perineal post 5, whereby to optimize the geometry of the fulcrum against which the leg of the patient is levered so as to provide improved distraction. Thus, perineal post 5 can be considered to have a "dynamic" construction, in the sense that second portion 15 is configured to be selectively moved away from first portion 10 so as to directly apply a distracting force to the patient's leg and/or to modify the geometry of the perineal post so as to optimize the geometry of the fulcrum against which the leg of the patient is levered and thereby provide improved distraction.

Figure 18:
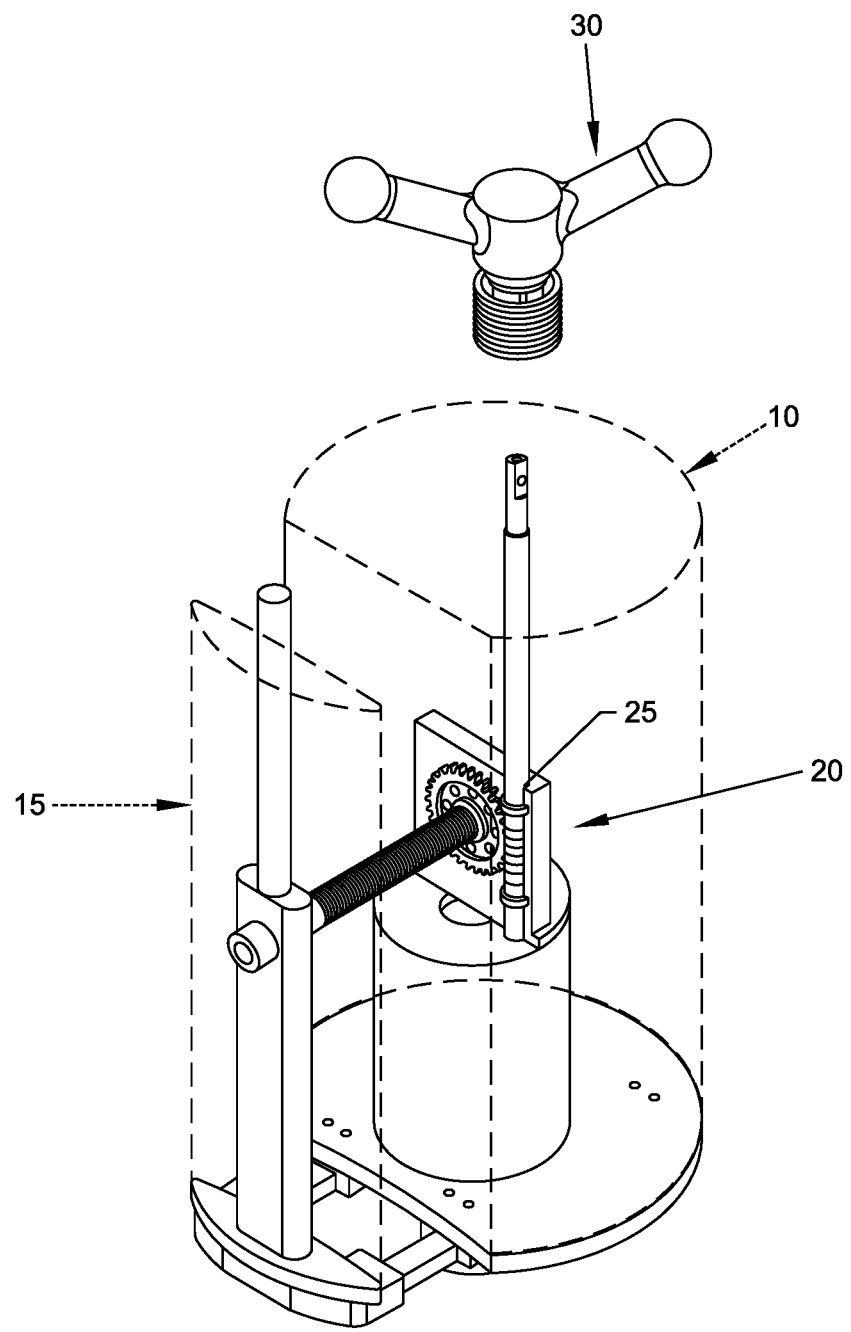
Figure 19:
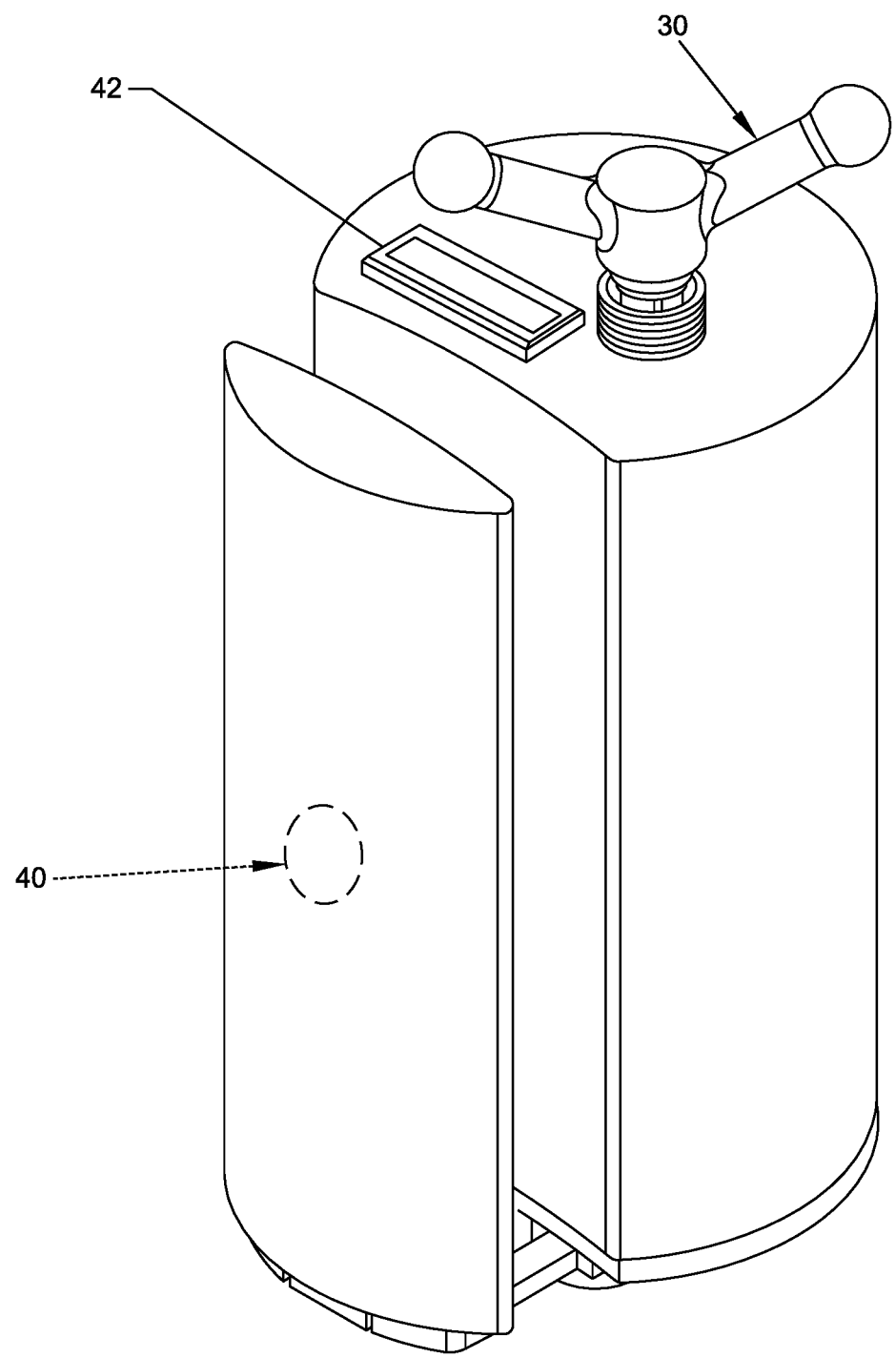
Figure 20:
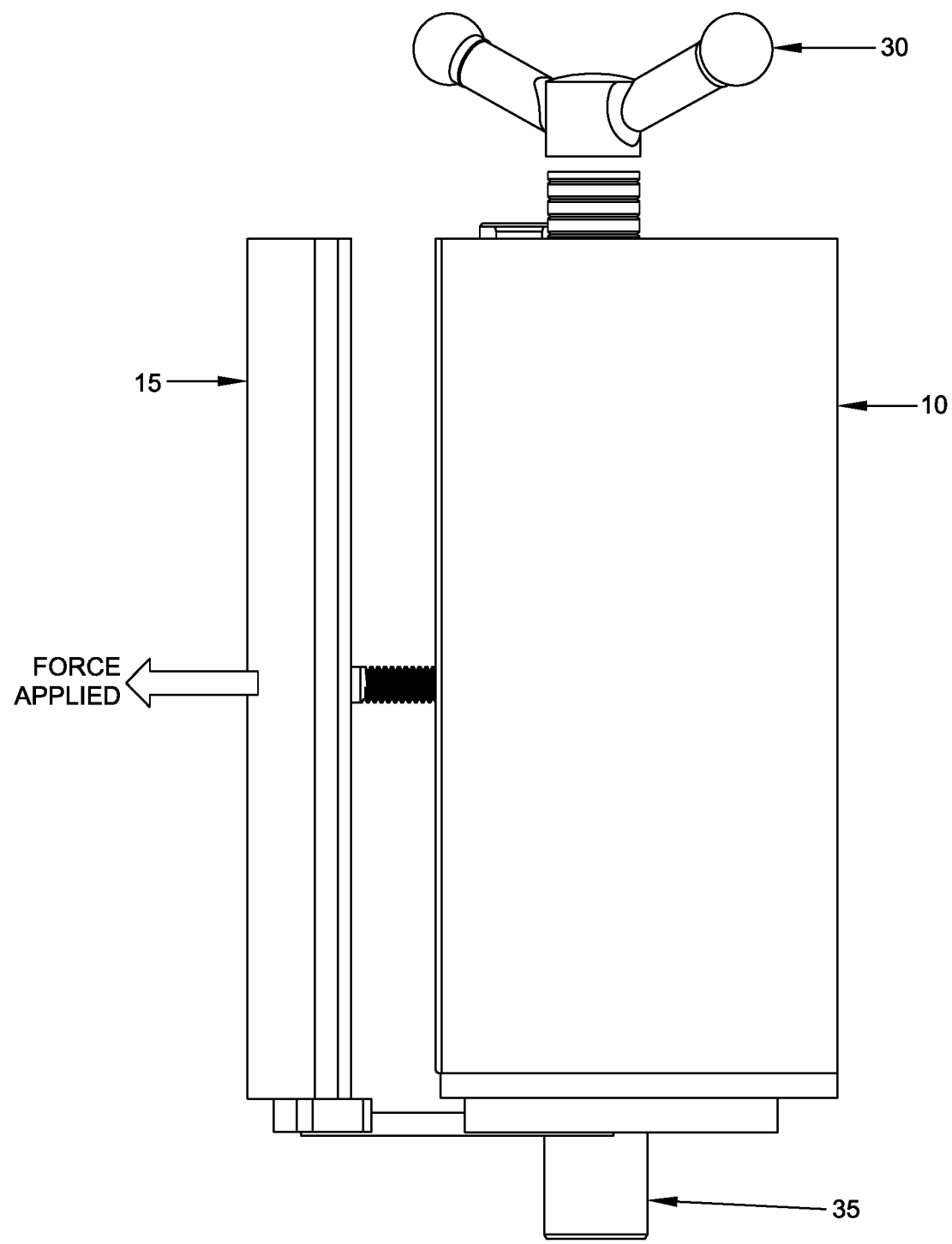
Figure 21:
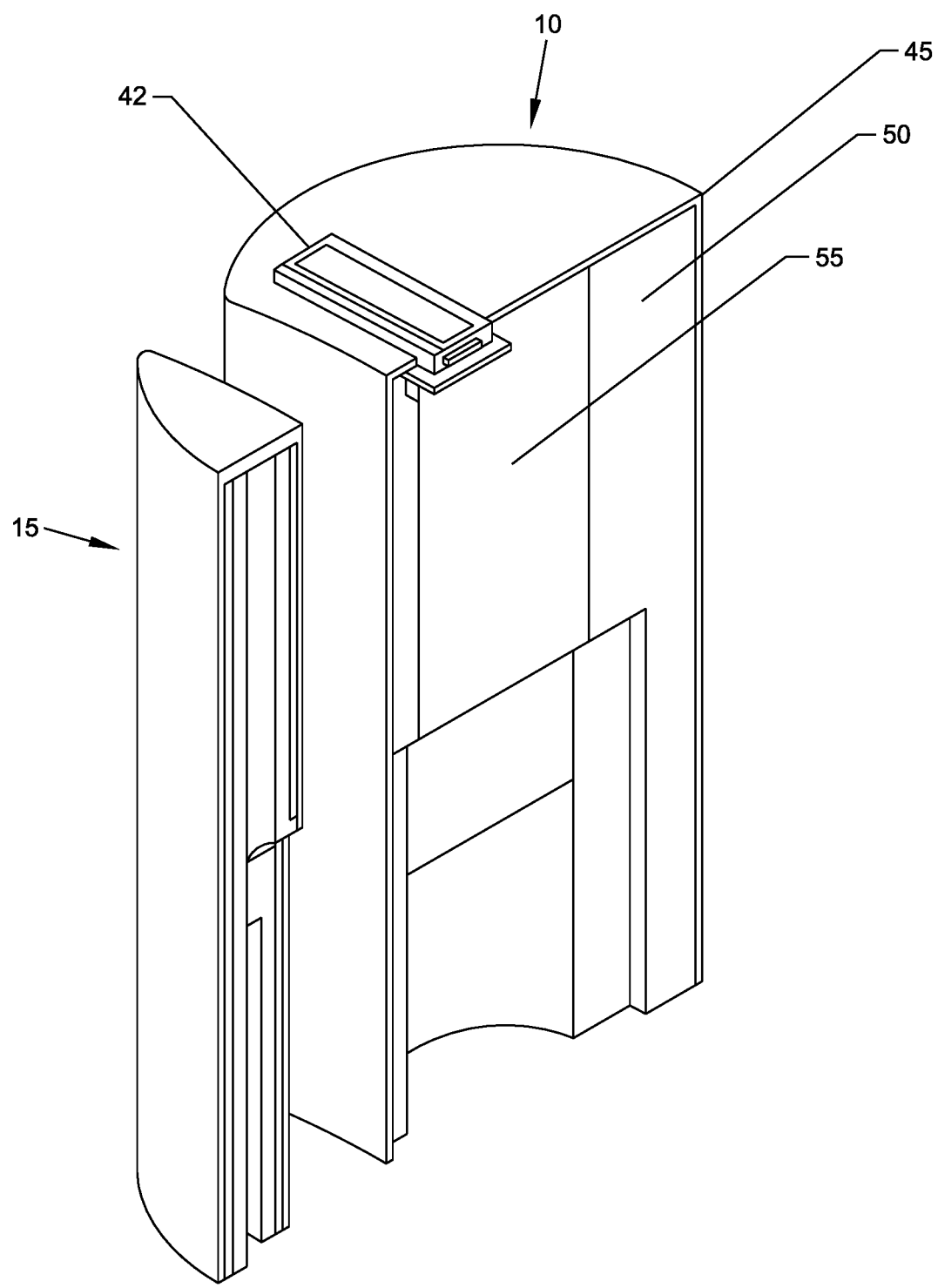
Figure 22:
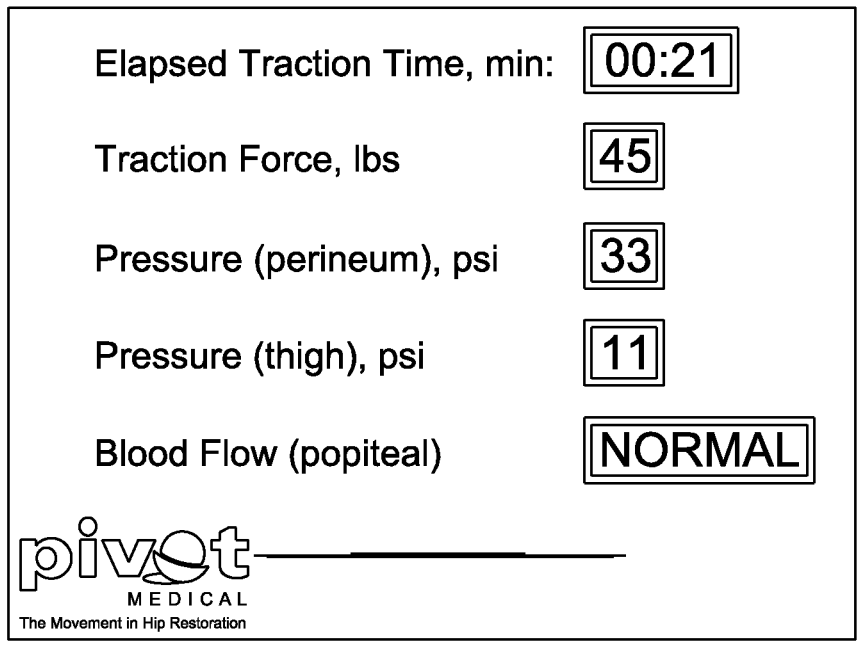
FIGS. 22-29 are schematic views showing exemplary displays showing the monitoring of various conditions commonly of interest to the surgeon.
Figure 23:
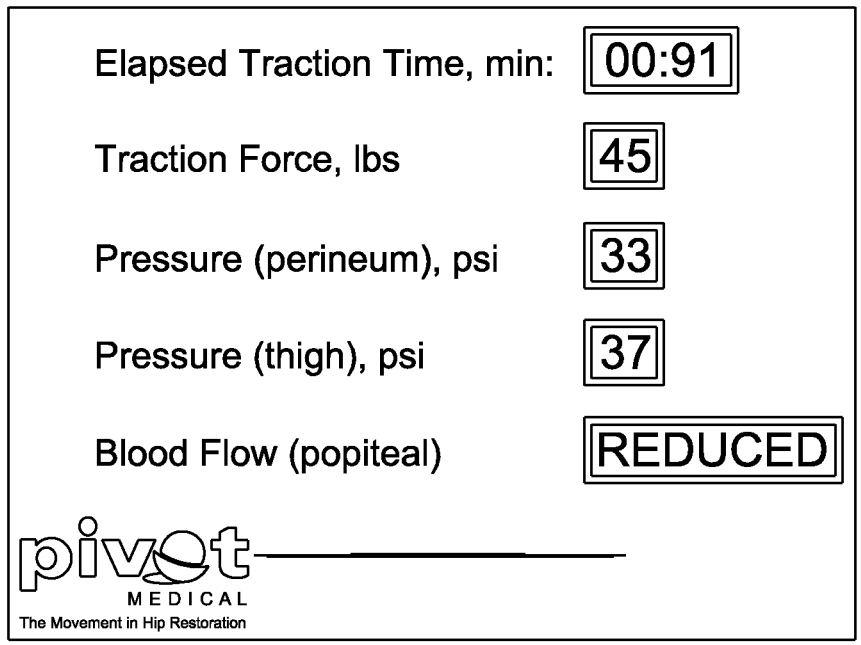
Figure 24:
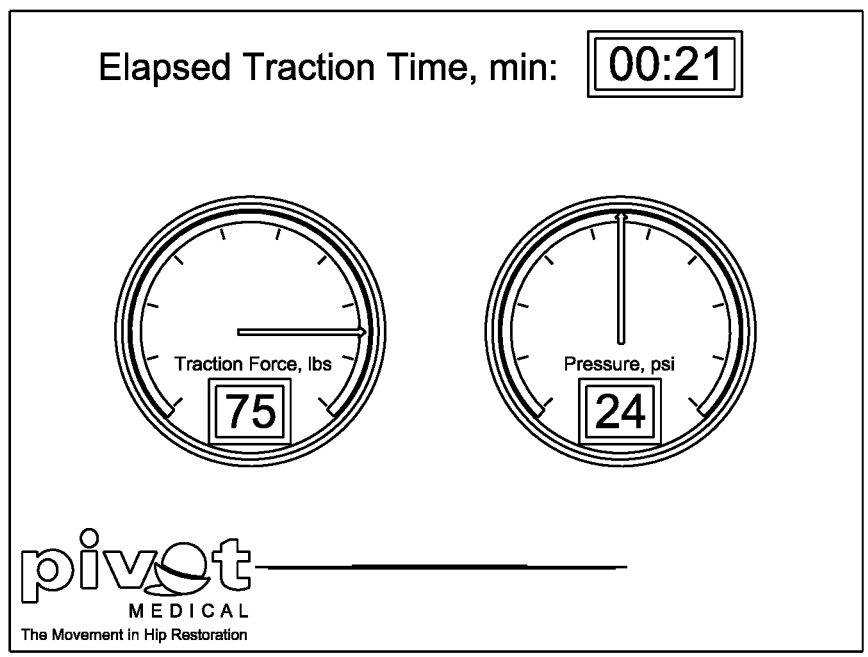
Figure 25:
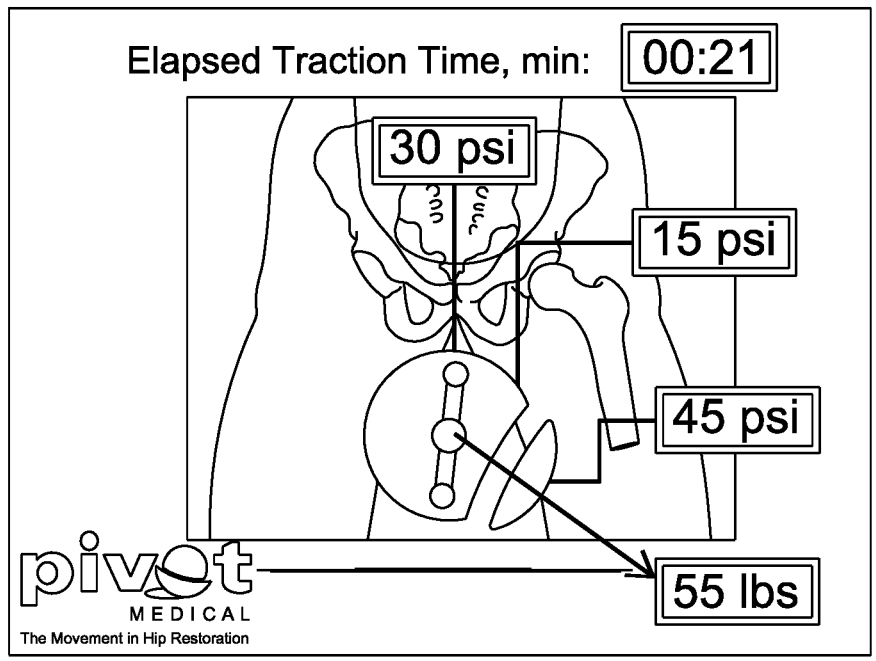
Figure 26:
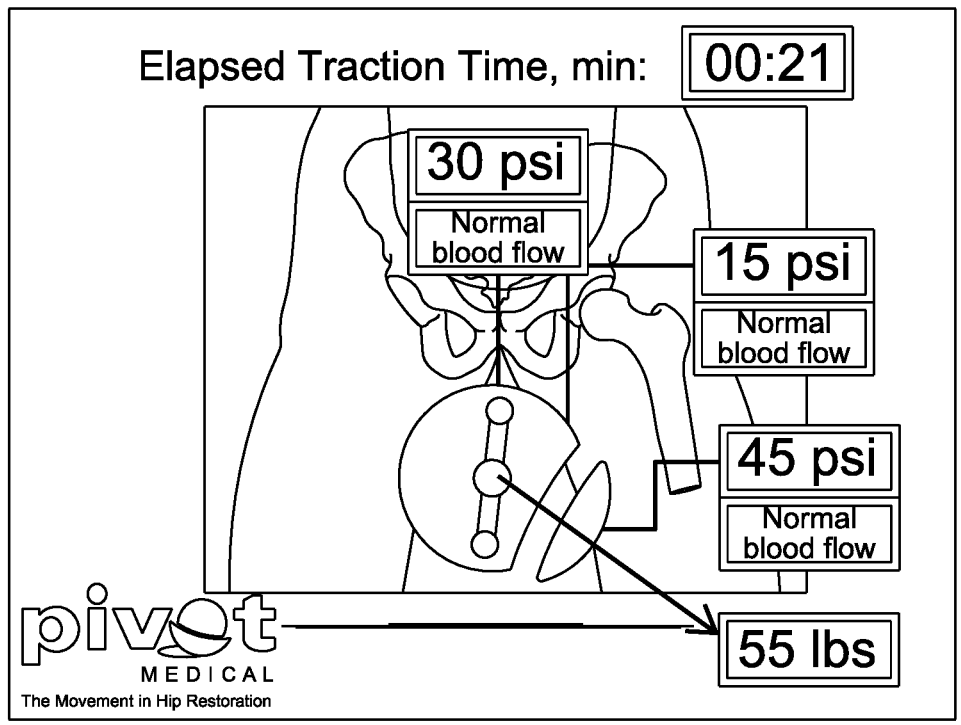
Figure 27:
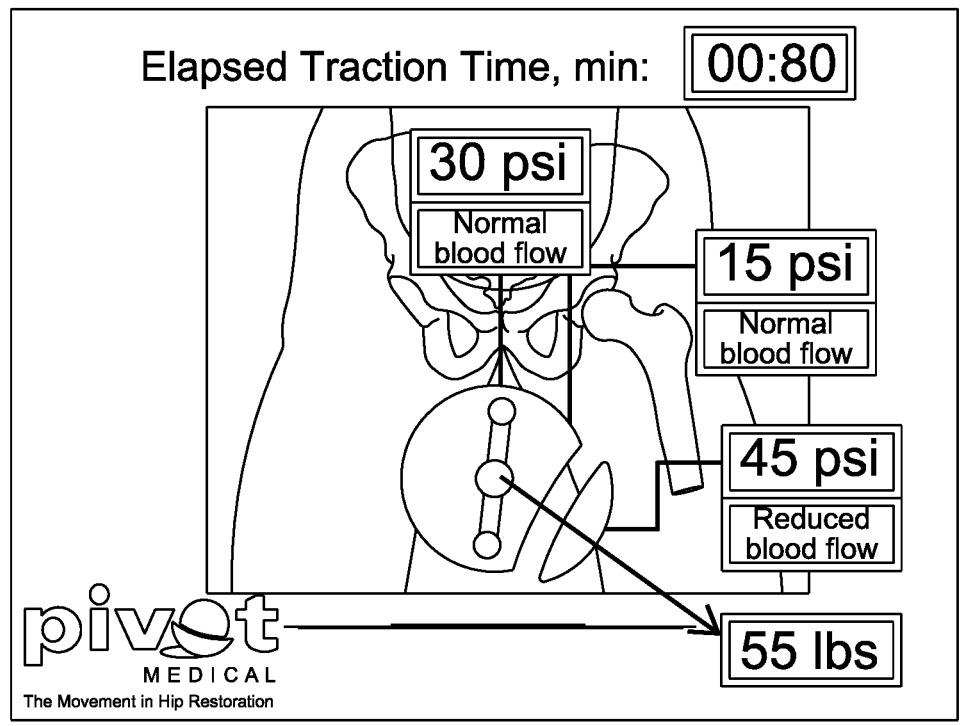
Figure 28:
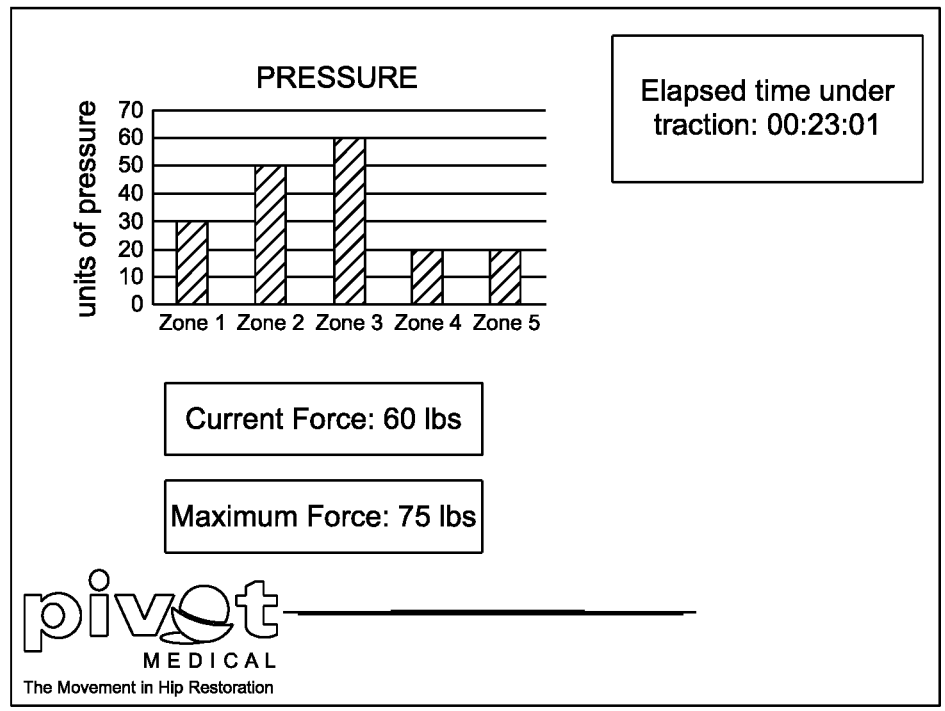
Figure 29:
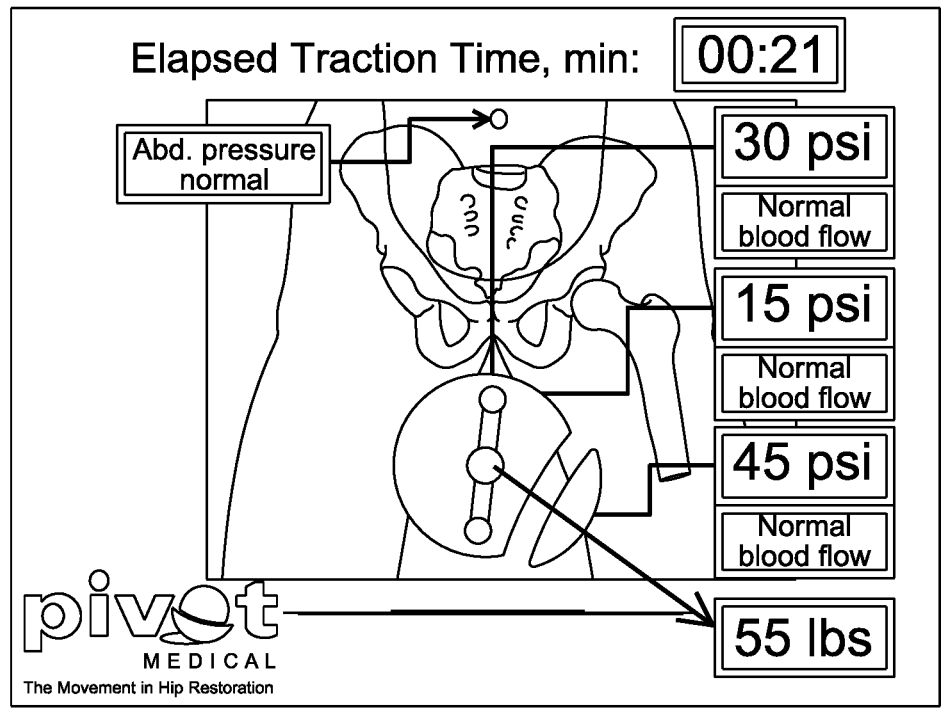
Figure 30:
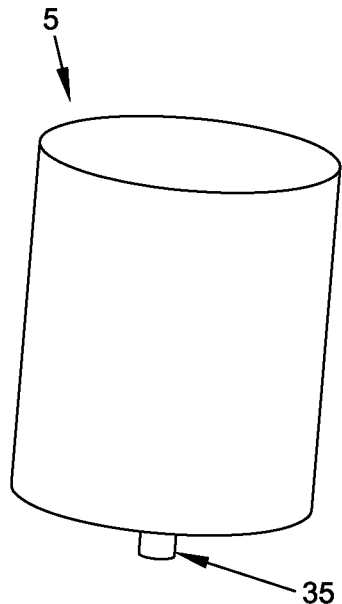
FIGS. 30-33 are schematic views showing a "static" perineal post formed in accordance with the present invention.
Figure 31:
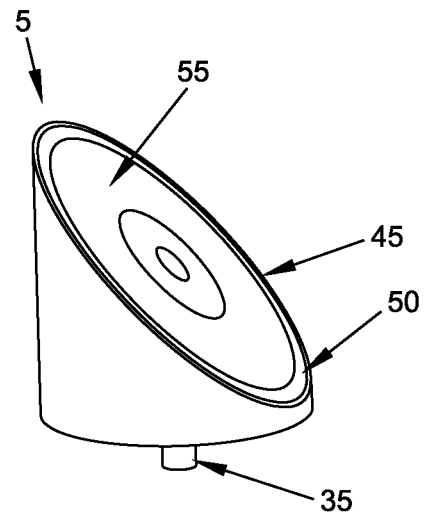

As seen in FIG. 18, perineal post 5 comprises an internal mechanism 20 for moving second portion 15 relative to first portion 10. Internal mechanism 20 may be any one of the various mechanisms known in the art for moving one member relative to another, e.g., internal mechanism 20 may comprise a worm gear system, a rack and pinion system, a lever system, a cam system, a hydraulic system, a pneumatic system, etc. By way of example but not limitation, and looking now at FIG. 18, internal mechanism 20 may comprise a worm gear drive 25 which is mounted to first portion 10 and which advances or retracts second portion 15 relative to first portion 10 when a handle 30 is turned. Alternatively, internal mechanism 20 may be powered by a motor which is directed by the surgeon using user interface controls of the sort well known in the art. In one form of invention, internal mechanism 20 is capable of creating and maintaining up to 150 lbs of force.

Preferably, perineal post 5 is pivotally mounted to the operating room table or fracture table via a pivot mount 35 (FIG. 20) so that the surgeon may rotate perineal post 5 about its longitudinal axis, whereby to adjust the direction along which second portion 15 travels, and hence to adjust the direction along which the distraction force is applied to the leg of the patient. This rotation of perineal post 5 may be done manually or under motor control.

If desired, perineal post 5 may also be configured so as to allow the surgeon to raise or lower perineal post 5 relative to the operating room table or fracture table, and hence relative to the patient. By way of example but not limitation, perineal post 5 may be secured to the operating room table or fracture table using a telescoping connection which is operated manually or under motor control.

In addition, if desired, perineal post 5 may be configured so as to allow the surgeon to selectively tilt perineal post 5 relative to the operating room table or fracture table, whereby to accommodate different positions of the patient's leg (e.g., abduction, adduction, flexion, extension, etc.). By way of example but not limitation, perineal post 5 may be secured to the operating room table or fracture table using a pivoting/tilting connection, e.g., a ball-and-socket joint. Again, this may be done manually or under motor control.

In one preferred form of the invention, controls are provided to allow the surgeon to (i) move second portion 15 of perineal post 5 relative to first portion 10 of perineal post 5, (ii) rotate perineal post 5 about its axis relative to the operating room table or fracture table, (iii) raise or lower perineal post 5 relative to the operating room table or fracture table, and (iv) tilt perineal post 5 relative to the operating room table or fracture table. In this way, the surgeon can establish and maintain a dislocating force on the hip joint, and/or modify the dislocating force on the hip joint during a procedure so as to allow the surgeon to change the operative view while viewing the interior of the hip joint with an endoscope.

Perineal post 5 preferably also includes one or more integrated sensors 40 (e.g., a sensor for measuring the pressure applied to a particular area of the anatomy), and the data from the one or more sensors 40 may be displayed on a screen 42 mounted to perineal post 5 or displayed on a separate device (not shown) such as a computer, a video monitor, a portable computing device, etc. The one or more integrated sensors 40 may monitor a wide range of pertinent conditions, e.g., the force applied to the patient's anatomy, the pressure applied to the patient's anatomy, the length of time traction has been applied to the patient's anatomy, the blood flow through the limb being distracted (e.g., via Doppler technology), the temperature of the patient's anatomy, changes in nerve conduction in the patient's limb (e.g., via evoked somatosensory nerve conduction), the quantity and flow rate of saline introduced into the hip joint and removed from the hip joint during the procedure, the vital signs of the patient, etc. FIGS. 22-29 are examplary displays showing the monitoring of various conditions commonly of interest to the surgeon.

It should also be appreciated that data from sensor(s) 40 may be used by the surgeon (or operating room staff) as guidance in order to make adjustments to perineal post 5. By way of example but not limitation, pressure data from sensor(s) 40 can be monitored in order to keep the force that the perineal post 5 is placing on the patient below a threshold level. Data from sensor(s) 40 can also be monitored in order to keep the vascular blood flow above a threshold level.

It should be appreciated that where perineal post 5 comprises the aforementioned controls for operating perineal post 5 and where perineal post 5 comprises the aforementioned integrated sensor(s) 40, computer means may be provided for operating the aforementioned controls based on the data acquired by sensor(s) 40 so that the force applied to the leg of the patient may be maintained at a predetermined level established by the surgeon.

Perineal post 5 preferably comprises a fabric cover 45 which overlies internal foam padding. In one preferred form of the invention, the internal foam padding is variable in density in order to protect delicate areas of the patient's anatomy while still allowing appropriate force to be applied to the patient's anatomy. By way of example but not limitation, and looking now at FIG. 21, the internal foam padding may comprise a portion 50 of low density foam (e.g., soft foam) for contacting the patient's perineum so as to reduce pressure on the nerves at that location, and a portion 55 of higher density foam (e.g., harder foam) to transfer the distraction forces to anatomy which is better able to accommodate the distraction forces.

Passive Perineal Post

If desired, perineal post 5 may have a "passive" construction, in the sense that it does not have a second portion 15 which is movable relative to a first portion 10. In this form of the invention, and looking now at FIGS. 30-33, perineal post 5 preferably comprises concentric layers of different densities of foam, wherein a softer, more compliant layer 50 (formed out of softer foam) is preferably disposed on the exterior of perineal post 5 (beneath fabric cover 45) and a denser, less compliant layer 55 (formed out of harder foam) is preferably disposed on the interior of perineal post 5.

Figure 32:
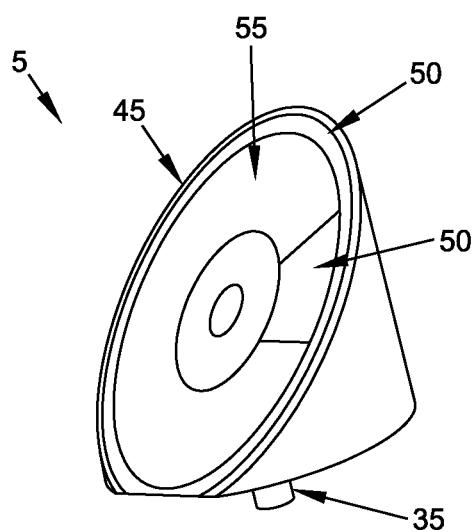
Figure 33:
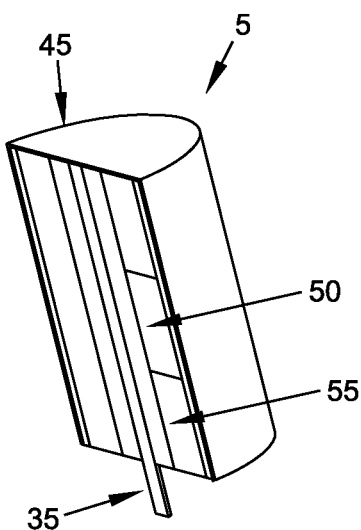

Alternatively and/or additionally, and looking now at FIGS. 32 and 33, sections of the denser, less compliant foam 55 may be cut away and replaced with sections of a less dense foam 50, thereby providing "windows" of lower densities of foam for contacting sensitive anatomy.

Perineal Post with at Least One Buttress

If desired, and looking now at FIGS. 34-38, perineal post 5 (either the "dynamic" perineal post 5 shown in FIGS. 17-21, or the "passive" perineal post 5 shown in FIGS. 30-33) may be used in conjunction with a buttress 60 (or series of buttresses 60) for constraining the anatomy so that the distraction forces generated by perineal post 5 can be more efficiently applied to the hip. Multiple buttresses provide a larger contact area on the patient, thus reducing the pressure on the patient's anatomy and thereby reducing potential damage to neurovascular structures. It will be appreciated that if multiple buttresses 60 are used, the multiple buttresses can be placed at different areas of the patient's anatomy to provide superior distraction for the hip joint.

Figure 34:
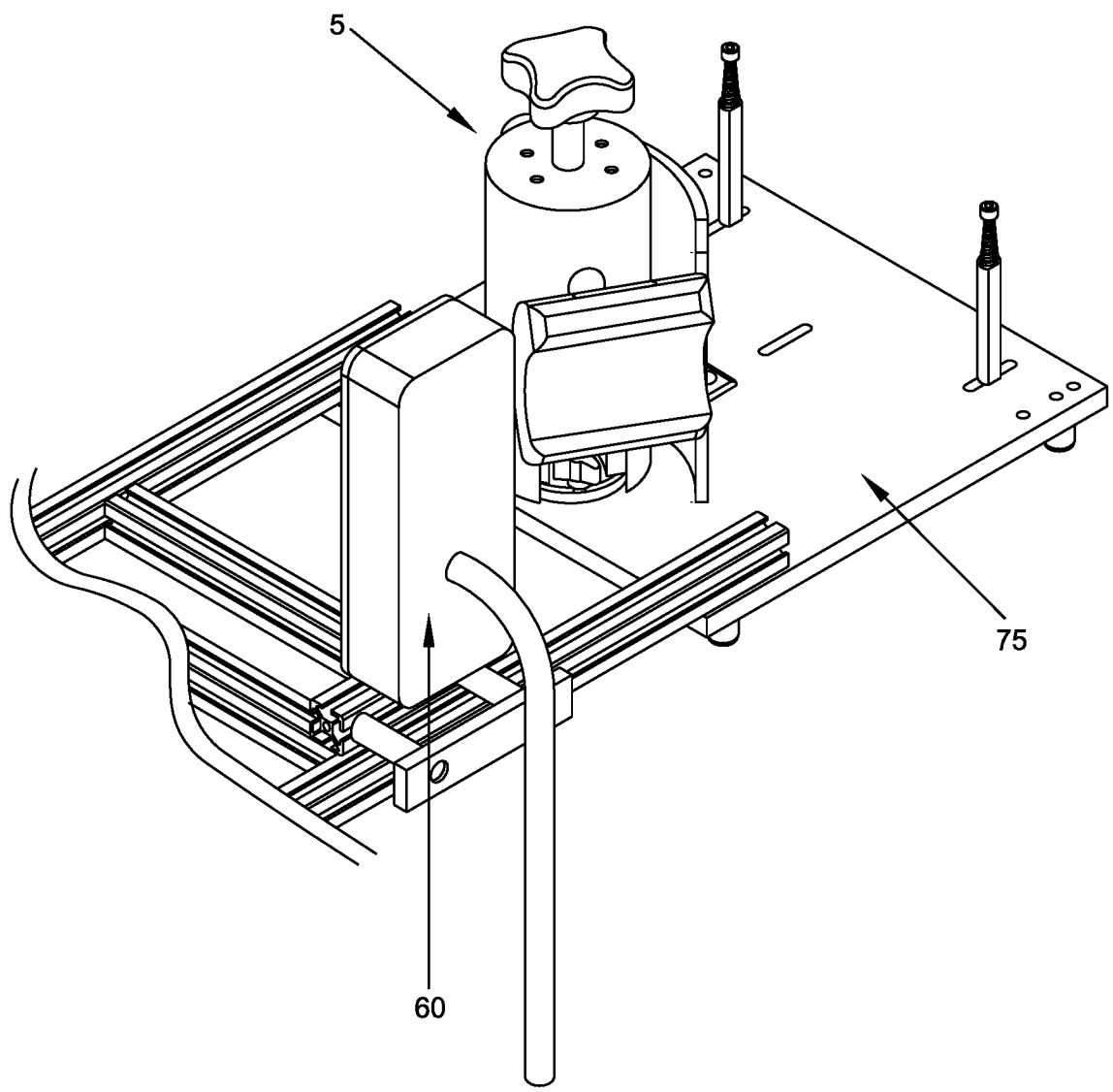
FIGS. 34-38 are schematic views showing a perineal post used in conjunction with a buttress.
Figure 35:
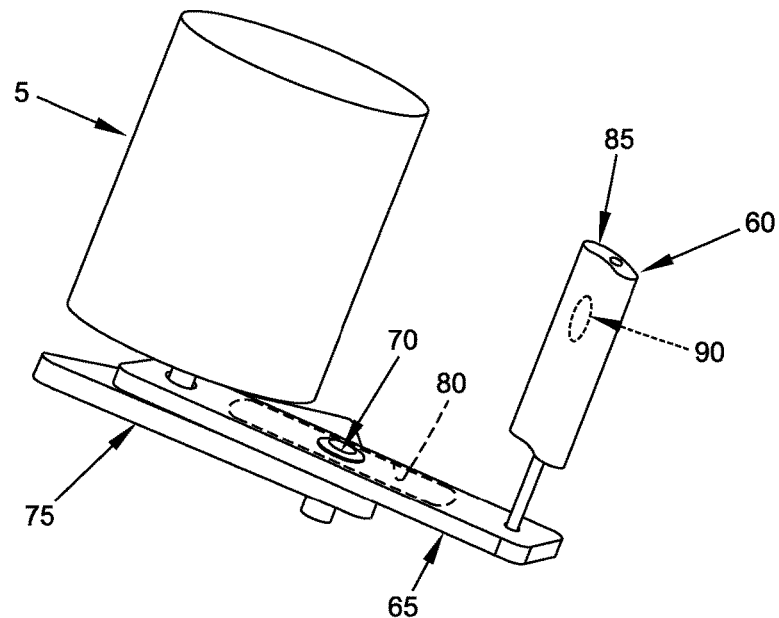
Figure 36:
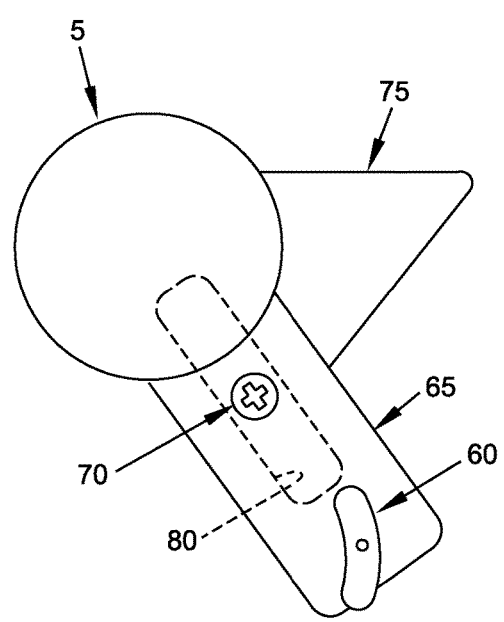
Figure 37:
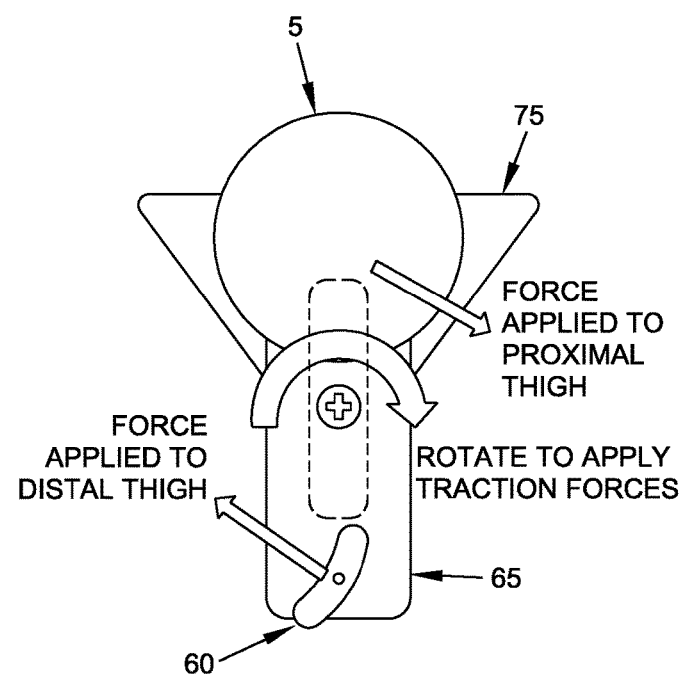
Figure 38:
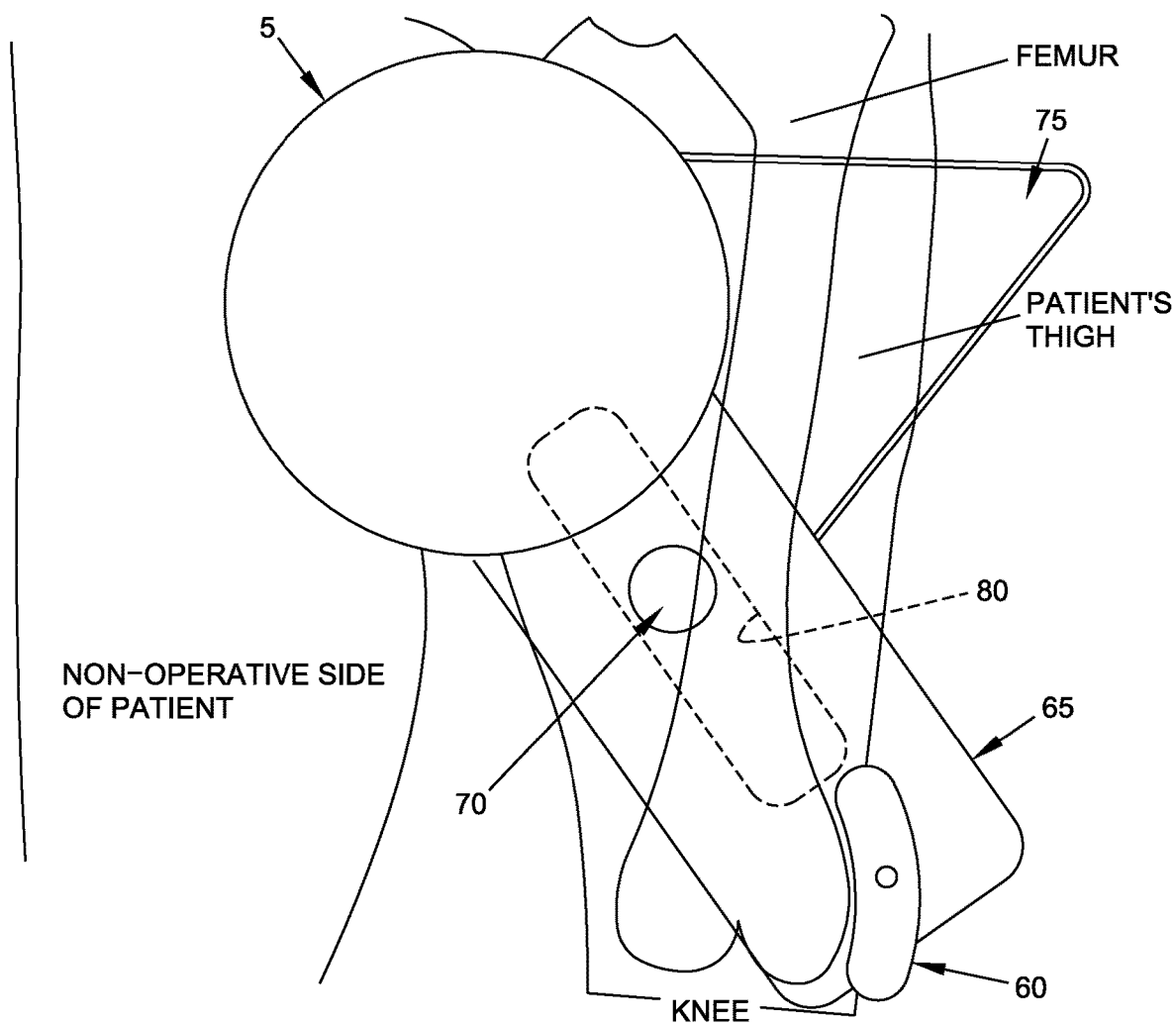

In one preferred form of the invention, and looking now at FIG. 34, perineal post 5 and the one or more buttresses 60 are separately mounted to the operating room table or fracture table. In this form of the invention, where perineal post 5 dynamically applies a distraction force to the leg of the patient, buttress(es) 60 provide(s) counter-pressure to the leg, thereby preventing the leg from abducting. In other words, the lateral force that perineal post 5 applies to the leg is counteracted by the buttress(es) 60, but at a location which allows the hip joint to distract. Buttress(es) 60 is/are preferably positioned on the lateral side of the distal thigh of the patient.

In another preferred form of the invention, and looking now at FIGS. 35-38, perineal post 5 and a buttress 60 are provided as a combined mechanism. More particularly, perineal post 5 and buttress 60 are mounted to a base 65 for connection (via a pivot 70) to operating room table or fracture table 75. Perineal post 5 and buttress 60 are preferably located at opposite ends of base 65, with pivot 70 being disposed between perineal post 5 and buttress 60. In this form of the invention, forces may be applied to the patient's leg simultaneously by both perineal post 5 and buttress 60, i.e., forces are applied to the patient's leg by rotating plate 65 (and hence perineal post 5 and buttress 60) around pivot 70.

By way of example but not limitation, in use, the patient is positioned supine on operating room table or fracture table 75, with perineal post 5 positioned between the patient's legs (i.e., on the medial side of the proximal thigh of the patient) and buttress 60 is positioned against the lateral side of the distal thigh of the patient. The surgeon then rotates base 65 about pivot 70 so as to push perineal post 5 laterally (i.e., to create a laterally-directed force) against the proximal thigh of the patient. By this action, buttress 60 simultaneously pushes the distal thigh medially (i.e., so as to create a medially-directed force). The combined forces applied to the patient's leg via perineal post 5 and buttress 60 facilitate distraction of the patient's hip.

If desired, the position of pivot 70 relative to perineal post 5 and buttress 60 can be varied (e.g., by moving pivot 70 within slot 80) in order to preferentially increase the rate at which the force is directed through either perineal post 5 or buttress 60. As pivot 70 moves closer to one of perineal post 5 or buttress 60, rotation of plate 65 about pivot 70 will preferentially move the other of perineal post 5 and buttress 60 a greater distance.

It should also be appreciated that buttress(es) 60 are preferably covered with a fabric cover 85 which overlies internal foam padding (not shown). In one preferred form of the invention, the internal foam padding is variable in density in order to protect delicate areas of the patient's anatomy while still allowing appropriate force to be applied to the patient's anatomy. By way of example but not limitation, the foam padding may comprise a portion of low density (e.g., soft) foam for contacting the patient's anatomy so as to reduce pressure on the anatomy, and a portion of higher density (e.g., harder) foam to transfer the distraction forces to anatomy which is better able to accommodate the distraction forces.

While the present invention has been discussed in the context of using buttress(es) 60 along the leg for distracting the hip joint, it should also be appreciated that buttress(es) 60 may be used on other areas of the patient's anatomy (e.g., the knee, the pelvis, etc.) to control the direction of the distraction forces and to control the pressure points created by the distraction forces on the patient's anatomy. By way of example but not limitation, buttress(es) 60 may be directed against the knee so as to help focus the distraction forces applied to the hip joint.

If desired, buttress(es) 60 may include one or more integrated sensors 90 (e.g., a sensor for measuring the pressure applied to a particular area of the anatomy), and the data from the one or more sensors 90 may be displayed on the screen 42 mounted to perineal post 5 or displayed on a separate device (not shown) such as a computer, a video monitor, a portable computing device, etc. The one or more integrated sensors 90 may monitor a wide range of pertinent conditions, e.g., the force applied to the patient's anatomy, the pressure applied to the patient's anatomy, the length of time traction has been applied to the patient's anatomy, the blood flow through the limb being distracted (e.g., via Doppler technology), the temperature of the patient's anatomy, changes in nerve conduction in the patient's limb (e.g., via evoked somatosensory nerve conduction), the quantity and flow rate of saline introduced into the hip joint and removed from the hip joint during the procedure, the vital signs of the patient, etc.

Knee Distraction Device

Figure 39:
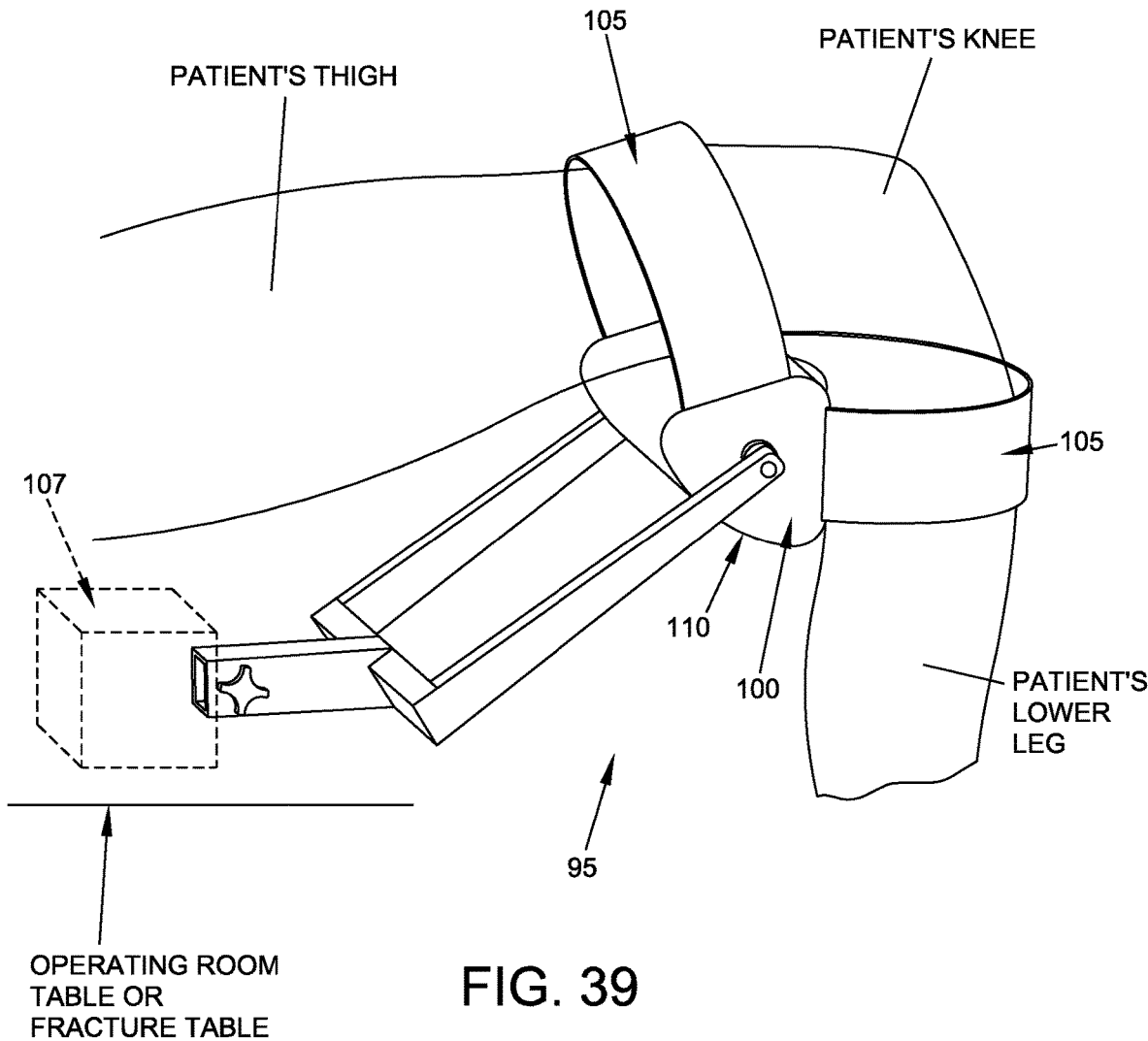
FIGS. 39-41 are schematic views showing a novel knee distraction device formed in accordance with the present invention.
Figure 40:
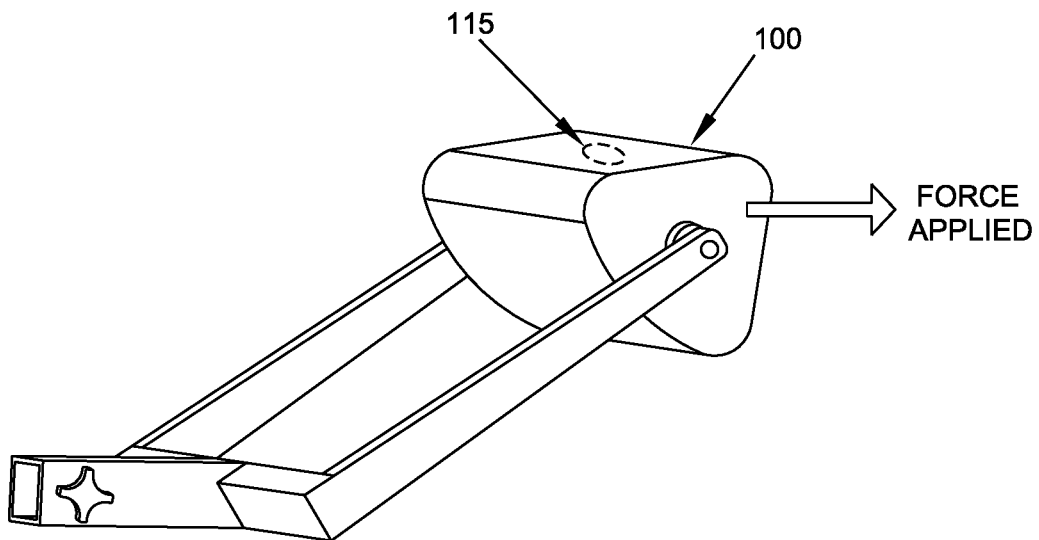
Figure 41:
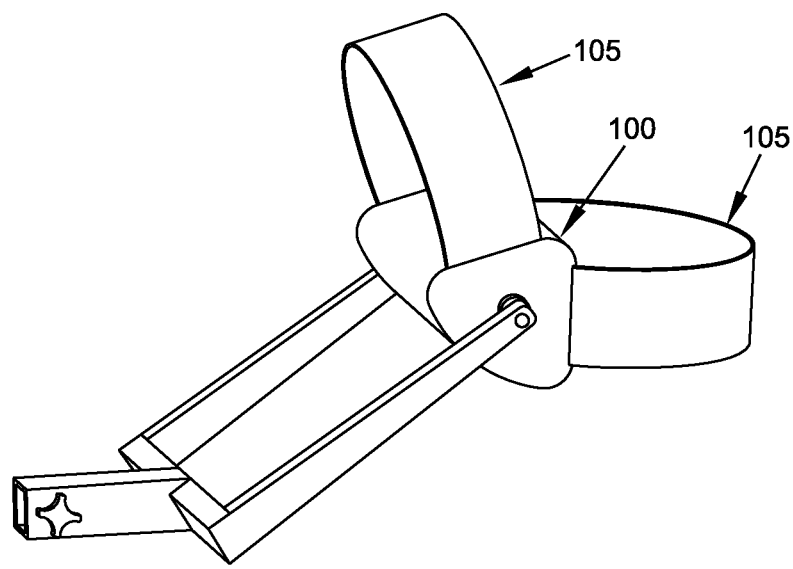

In accordance with the present invention, and looking now at FIGS. 39-41, a knee distraction device 95 may also be provided to effect hip distraction. Knee distraction device 95 may be used alone or in combination with the aforementioned perineal post 5 (either "dynamic" as shown in FIGS. 17-21, or "passive" as shown in FIGS. 30-33) and/or in combination with the aforementioned buttress(es) 60.

In this form of the invention, knee distraction device 95 is mounted to the operating room table or fracture table, and the patient is positioned supine on the operating room table or fracture table, with the patient's leg being set on a support 100 of knee distraction device 95. Straps 105 are then used to secure the patient's leg to knee distraction device 95. Knee distraction device 95 is manipulated so as to transmit forces to the patient's leg, whereby to create distally-directed distraction of the femur and thereby distract the hip joint. This is accomplished through a positioning mechanism 107 which is located between support 100 of knee distraction device 95 and the operating room table or fracture table. Knee distraction device 95 preferably pivots relative to operating room table or traction table so as to provide the ability to extend, flex, adduct and abduct the leg. Positioning mechanism 107 is preferably located at base of knee distraction device 95 (i.e., where knee distraction device 95 mounts to operating room table or fracture table) such as is shown in FIG. 39. Alternatively, positioning mechanism 107 may be incorporated into knee distraction device 95 at a location between support 100 and the table mounting location. Positioning mechanism 107 comprises hinges, a ball-and-socket joint or other mechanisms known in the art for allowing support 100 of knee distraction device 95 to be selectively positioned relative to the operating room table or fracture table. Again, the distraction provided by knee distraction device 95 may be in addition to the distraction provided by perineal post 5 and/or buttress(es) 60, or may be the sole means for applying distraction forces to the hip joint.

It should be appreciated that support 100 is preferably covered with a fabric cover 110 which overlies internal foam padding (not shown). In one preferred form of the invention, the internal foam padding is variable in density in order to protect delicate areas of the patient's anatomy while still allowing appropriate force to be applied to the patient's anatomy. By way of example but not limitation, the foam padding may comprise a portion of low density (e.g., soft) foam for contacting the patient's anatomy so as to reduce pressure on the anatomy, and a portion of higher density (e.g., harder) foam to transfer the distraction forces to anatomy which is better able to accommodate the distraction forces.

If desired, support 100 may include one or more integrated sensors 115 (e.g., a sensor for measuring the pressure applied to a particular area of the anatomy), and the data from the one or more sensors 115 may be displayed on the screen 42 mounted to perineal post 5 or displayed on a separate device (not shown) such as a computer, a video monitor, a portable computing device, etc. The one or more integrated sensors 115 may monitor a wide range of pertinent conditions, e.g., the force applied to the patient's anatomy, the pressure applied to the patient's anatomy, the length of time traction has been applied to the patient's anatomy, the blood flow through the limb being distracted (e.g., via Doppler technology), the temperature of the patient's anatomy, changes in nerve conduction in the patient's limb (e.g., via evoked somatosensory nerve conduction), the quantity and flow rate of saline introduced into the hip joint and removed from the hip joint during the procedure, the vital signs of the patient, etc.

Combination of Perineal Post, Buttress(es) and Knee Distraction Device

As noted above, hip distraction may be achieved using a combination of perineal post 5 (either "dynamic" as shown in FIGS. 17-21, or "passive" as shown in FIGS. 30-33), buttress(es) 60 and/or knee distraction device 95.

It will be appreciated that the present invention provides a new and improved approach for distracting the hip joint which addresses one or more of the problems associated with the prior art.

Among other things, the new and improved approach of the present invention:

creates a distracted space of significant size so as to allow for treatment of the central compartment of the hip joint;

minimizes the pressure applied to soft tissue, nerve and vascular structures, and thereby minimizes the risk of nerve palsies and thrombosis;

minimizes the forces transmitted through other healthy anatomical structures such as the knee and ankle, thereby minimizing the risk of complications;

more efficiently focuses the traction forces on the hip joint;

allows for variation in the applied traction vector so as to (i) accommodate patients with differences in anatomy (i.e., differences in boney structure, the strength of soft tissue, the tension of capsule tissue, etc.), and (ii) provide surgical access to different parts of the hip joint (i.e., anterior, posterior and lateral regions)—thereby effectively resulting in customized traction for each patient;

provides an apparatus with a more intuitive way to apply traction, utilizing simple controls to apply/remove traction during a procedure; and/or provides the surgeon with feedback during the procedure, so that the surgeon can better understand the effects of traction and the procedure on the patient (e.g., the traction force applied, pressure on anatomy, blood flow to the leg, temperature of the tissue, extravasation of flushing fluid from the hip joint, changes in nerve conduction, time under traction, etc.).

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for distracting a hip joint of a patient, said apparatus comprising:
    a perineal post for engagement with a leg of the patient, wherein the perineal post comprises a first portion and a second portion, wherein the second portion is configured to move relative to the first portion while the first portion remains in a fixed position, and further wherein the second portion of the perineal post is configured to be moved diagonally away from the first portion of the perineal post so as to directly apply a pushing force to the leg of the patient, wherein the pushing force is applied by the second portion of the perineal post to distract the hip joint.

2. The apparatus according to claim 1 further comprising an element for holding the leg distal to the perineal post while the pushing force is being applied to the leg of the patient.

3. Apparatus according to claim 1 further comprising a mechanism for moving the second portion of the perineal post relative to the first portion of the perineal post.

4. Apparatus according to claim 3 wherein the mechanism is a manually-operated mechanism.

5. Apparatus according to claim 3 wherein the mechanism is a motorized mechanism.

6. Apparatus according to claim 1 further comprising at least one sensor for sensing a condition relating to the patient.

7. Apparatus according to claim 6 wherein the at least one sensor is disposed on the second portion of the perineal post.

8. Apparatus according to claim 6 wherein the at least one sensor is configured to sense one from the group consisting of: force applied to the patient, pressure applied to the patient, length of time that distraction has been applied to the patient, blood flow through a leg of the patient, temperature of the patient, and nerve conduction within a leg of the patient.

9. Apparatus according to claim 6 further comprising a display for presenting data acquired by the at least one sensor.

10. Apparatus according to claim 9 wherein the display is mounted to the first portion of the perineal post.

11. A method for distracting a hip joint of a patient, the method comprising:
    mounting a perineal post to a table, wherein the perineal post comprises a first portion and a second portion, wherein the second portion is configured to move relative to the first portion while the first portion remains in a fixed position;
    positioning the patient on the table so that a leg of the patient is in a distraction position;
    diagonally moving the second portion of the perineal post away from the first portion of the perineal post so as to directly apply a pushing force to the leg of the patient, wherein the pushing force applied by the diagonal movement of the second portion of the perineal post distracts the hip joint.

12. The method according to claim 11, further comprising holding the leg distal to the perineal post while applying the pushing force to the leg of the patient.

13. The method according to claim 11 further comprising providing a mechanism for moving the second portion of the perineal post away from the first portion.

14. The method according to claim 13 wherein the mechanism is a manually-operated mechanism.

15. The method according to claim 13 wherein the mechanism is a motorized mechanism.

16. The method according to claim 11 further comprising providing at least one sensor for sensing a condition relating to the patient.

17. The method according to claim 16 wherein the at least one sensor is disposed on the second portion of the perineal post.

18. The method according to claim 17 wherein the at least one sensor is configured to sense one from the group consisting of: force applied to the patient, pressure applied to the patient, length of time that distraction has been applied to the patient, blood flow through a leg of the patient, temperature of the patient, and nerve conduction within a leg of the patient.

19. The method according to claim 16 further comprising providing a display for presenting data acquired by the at least one sensor.

20. The method according to claim 19 wherein the display is mounted to the first portion of the perineal post.

* * * * *